United States Patent
Chang et al.

(10) Patent No.: US 9,854,987 B2
(45) Date of Patent: Jan. 2, 2018

(54) DISTRIBUTED, MINIMALLY-INVASIVE NEURAL INTERFACE FOR WIRELESS EPIDURAL RECORDING

(75) Inventors: Sun-Il Chang, Ann Arbor, MI (US); Euisik Yoon, Superior Township, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 733 days.

(21) Appl. No.: 13/503,196

(22) PCT Filed: Oct. 20, 2010

(86) PCT No.: PCT/US2010/053449
§ 371 (c)(1),
(2), (4) Date: Jul. 16, 2012

(87) PCT Pub. No.: WO2011/123150
PCT Pub. Date: Oct. 6, 2011

(65) Prior Publication Data
US 2012/0302856 A1    Nov. 29, 2012

Related U.S. Application Data

(60) Provisional application No. 61/253,141, filed on Oct. 20, 2009.

(51) Int. Cl.
*A61B 5/04* (2006.01)
*A61B 5/0478* (2006.01)
*A61B 5/00* (2006.01)

(52) U.S. Cl.
CPC .......... *A61B 5/0478* (2013.01); *A61B 5/0028* (2013.01); *A61B 5/7232* (2013.01)

(58) Field of Classification Search
CPC ...... A61N 1/08; A61N 1/0534; A61N 1/3605; A61N 1/3787; A61N 1/0531;
(Continued)

(56) References Cited

U.S. PATENT DOCUMENTS 5,319,738 A * 6/1994 Shima .................. G05B 13/027
706/25
6,210,417 B1   4/2001 Baudino et al.
(Continued)

OTHER PUBLICATIONS

Fayomi et al. "A 1-V, 10-bit Rail-to-Rail Successive Approximation Analog-to-Digital Converter in Standard 0.18μm CMOS Technology". May 2001.*
(Continued)

*Primary Examiner* — Joseph Stoklosa
*Assistant Examiner* — Brian M Antiskay
(74) *Attorney, Agent, or Firm* — Reising Ethington P.C.

(57) ABSTRACT

A neural interface for measuring or stimulating brain neural activity, either as a standalone unit or as a part of a larger system of similar neural interfaces. The neural interface includes a bolt-shaped housing having a tool-engaging head and threaded shank with internal circuitry and at least one electrode. In use, the housing is threaded into a cranial bore such that the electrode contacts the outer surface of the meninges. The neural interface circuitry includes an SAR ADC that provides at least rail-to-rail operation to convert received signals from the electrode(s) into digital data that can be modulated and wirelessly transmitted by intra-skin or other suitable communication.

20 Claims, 29 Drawing Sheets

(58) Field of Classification Search
CPC ............... A61N 1/0529; A61N 1/0539; A61N 1/37229; A61N 1/0526; A61N 1/059; A61B 5/6868; A61B 5/0006; A61B 5/0024; A61B 5/0482; A61B 5/165; A61B 5/0031; A61B 5/686; A61B 18/14
USPC ........ 600/372–373, 377–378, 382–383, 393, 600/544–545; 607/115–119
See application file for complete search history.

(56) References Cited

U.S. PATENT DOCUMENTS

| | | | |
|---|---|---|---|
| 6,415,184 B1* | 7/2002 | Ishikawa | A61N 1/3605 607/116 |
| 7,302,298 B2 | 11/2007 | Lowry et al. | |
| 7,548,775 B2 | 6/2009 | Kipke et al. | |
| 8,797,204 B2 | 8/2014 | Yoon et al. | |
| 8,922,274 B2 | 12/2014 | Yoon et al. | |
| 2004/0102828 A1* | 5/2004 | Lowry et al. | 607/116 |
| 2004/0243207 A1* | 12/2004 | Olson et al. | 607/116 |
| 2005/0021117 A1* | 1/2005 | He et al. | 607/116 |
| 2005/0090727 A1* | 4/2005 | Kurtz et al. | 600/372 |
| 2005/0143790 A1* | 6/2005 | Kipke et al. | 607/60 |
| 2006/0173259 A1 | 8/2006 | Flaherty et al. | |
| 2009/0105784 A1* | 4/2009 | Massoud-Ansari et al. | 607/45 |
| 2009/0240131 A1* | 9/2009 | Lu et al. | 600/372 |
| 2009/0244014 A1 | 10/2009 | Hotelling et al. | |
| 2009/0253977 A1 | 10/2009 | Kipke et al. | |
| 2009/0319211 A1 | 12/2009 | Bresch | |
| 2010/0130844 A1 | 5/2010 | Williams et al. | |
| 2010/0156685 A1 | 6/2010 | Westwick et al. | |
| 2010/0198297 A1 | 8/2010 | Cogan et al. | |
| 2011/0193633 A1 | 8/2011 | Yoon et al. | |
| 2012/0218137 A1 | 8/2012 | Yoon et al. | |

OTHER PUBLICATIONS

A. B. Schwartz et al., "Brain-Controlled Interfaces:Movement Restoration with Neural Prosthetics," Neuron, vol. 52, pp. 205-220, 2006.

P. K. Campbell et al., "A Silicon-Based, Three-Dimensional Neural Interface: Manufacturing Processes for an Intracortical Electrode Array," Biomedical Engineering, IEEE Transactions on, vol. 38, No. 8, pp. 758-768, 1991.

K. D. Wise et al., "Microelectrodes, Microelectronics, and Implantable Neural Microsystems," Proceedings of the IEEE, vol. 96, No. 7, pp. 1184-1202, 2008.

R. Srinivasan et al., "Spatial Filtering and Neocortical Dynamics: Estimates of EEG Coherence," Biomedical Engineering, IEEE Transactions on, vol. 45, No. 7, pp. 814-826, 1998.

E. C. Leuthardt et al., "A Brain-Computer Interface Using Electrocorticographic Signals in Humans," Journal of Neural Engineering, vol. 1, pp. 63-71, 2004.

G. Schalk et al., "Two-Dimensional Movement Control Using Electrocorticographic Signals in Humans," Journal of Neural Engineering, vol. 5, pp. 75-84, 2008.

M. Slutzky et al., "Optimal Spatial Resolution of Epidural and Subdural Electrode Arrays for Brain-Machine Interface Applications," 30th Annual Intl. IEEE EMBS Conference, Vancouver, BC, Canada, 2008, pp. 3771-3774.

R. J. Vetter et al., "Development of a Microscale Implantable Neural Interface (MINI) Probe System," Proceedings of the 2005 IEEE, Engineering in Medicine and Biology 27th Annual Conference, Shanghai, China, 2005, pp. 7341-7344.

K. M. Al-Ashmouny et al., "IBCOM (Intra-Brain Communication) Microsystem: Wireless Transmission of Neural Signals within the Brain," 31st Annual International Conference of the IEEE EMBS, Minneapolis, MN, Sep. 2-6, 2009, pp. 2054-2057.

C. Chestek et al., "Wireless Multi-Channel Sensor for Neurodynamic Studies," 2004, pp. 915-918.

* cited by examiner

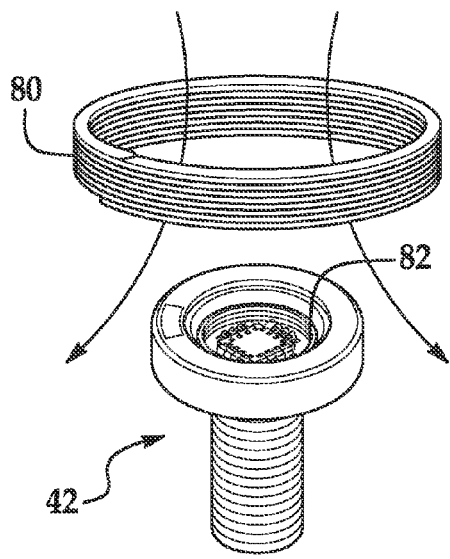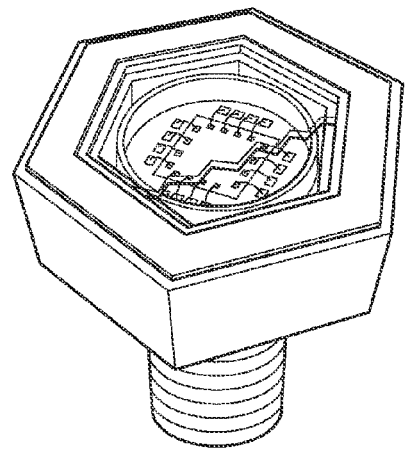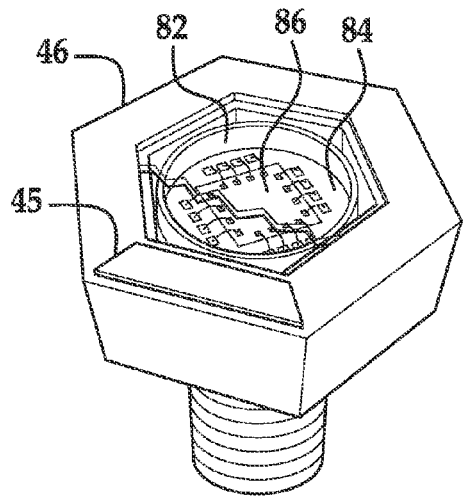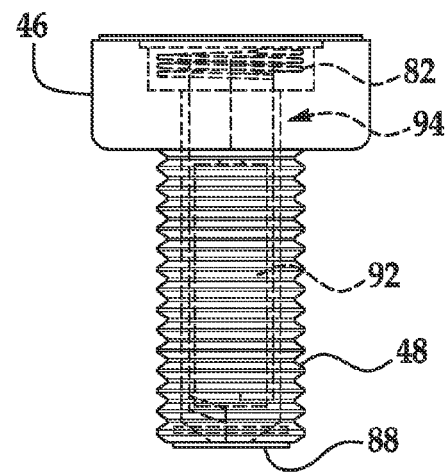
FIG. 6                FIG. 7A
FIG. 7B               FIG. 7C
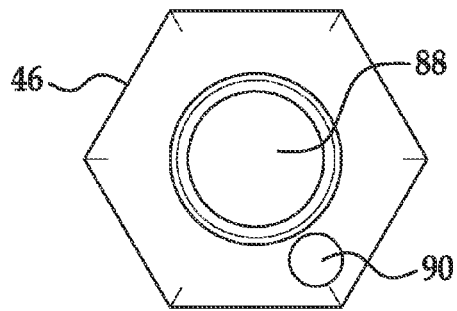
FIG. 7D

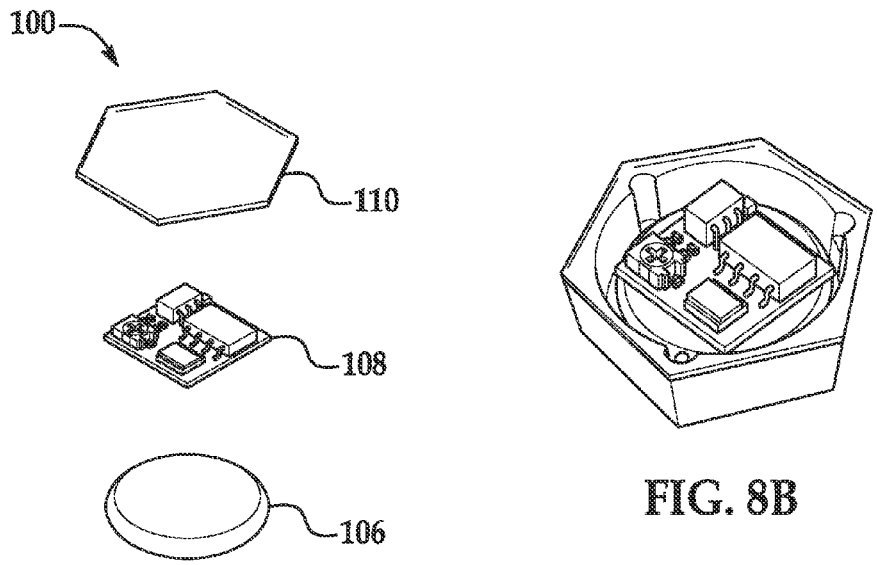
FIG. 8B
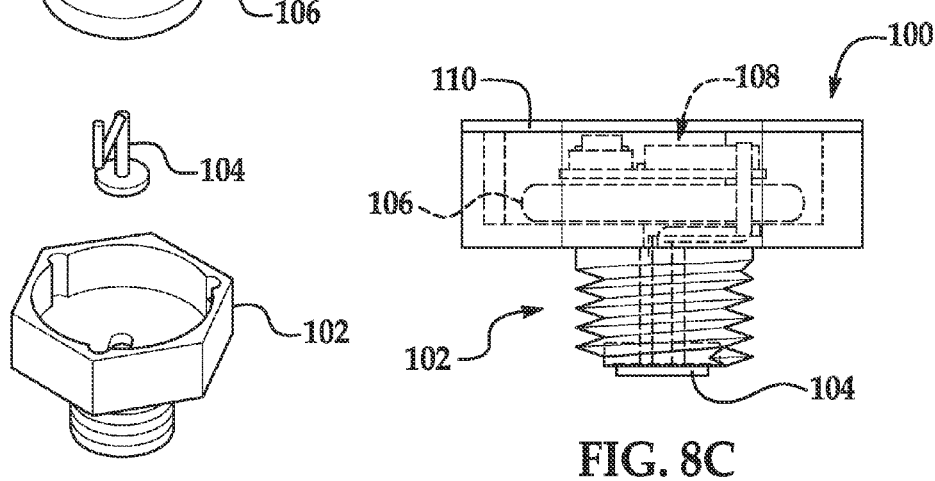
FIG. 8A
FIG. 8C
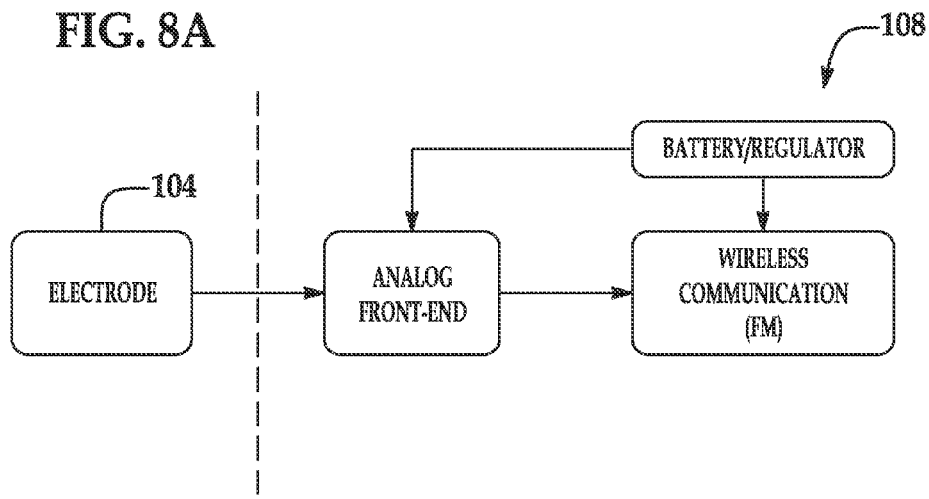
FIG. 9

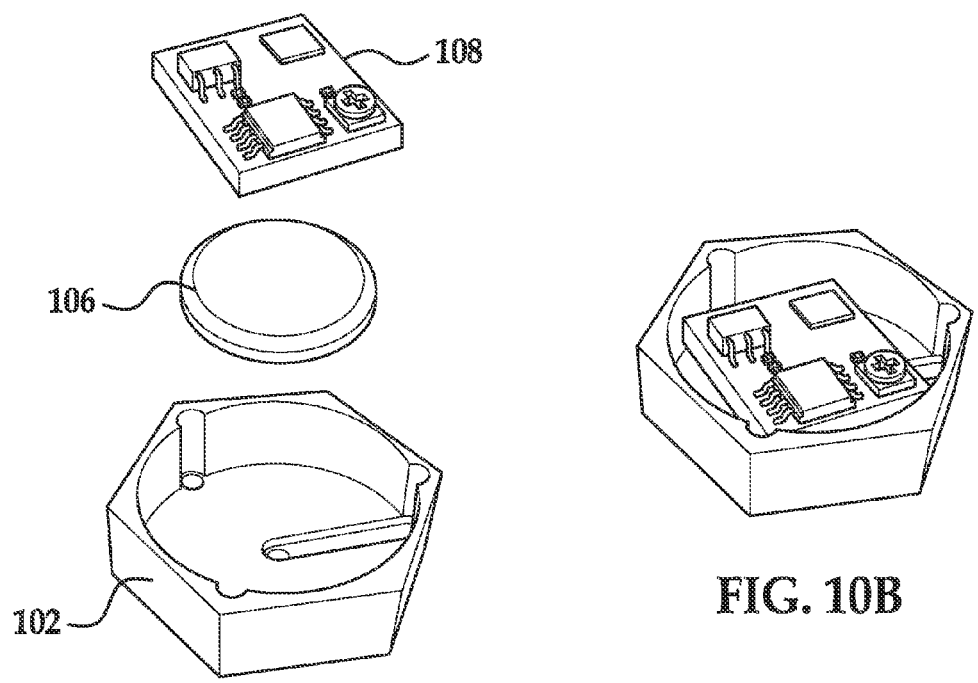
FIG. 10A
FIG. 10B
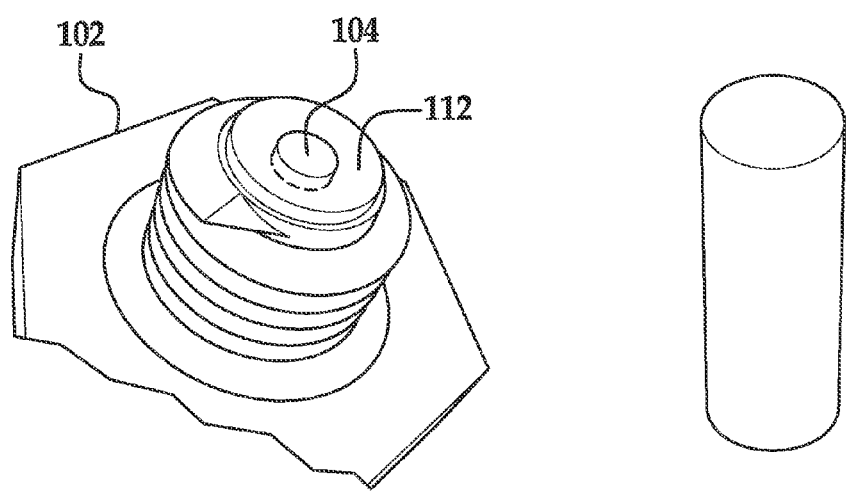
FIG. 11A
FIG. 11B

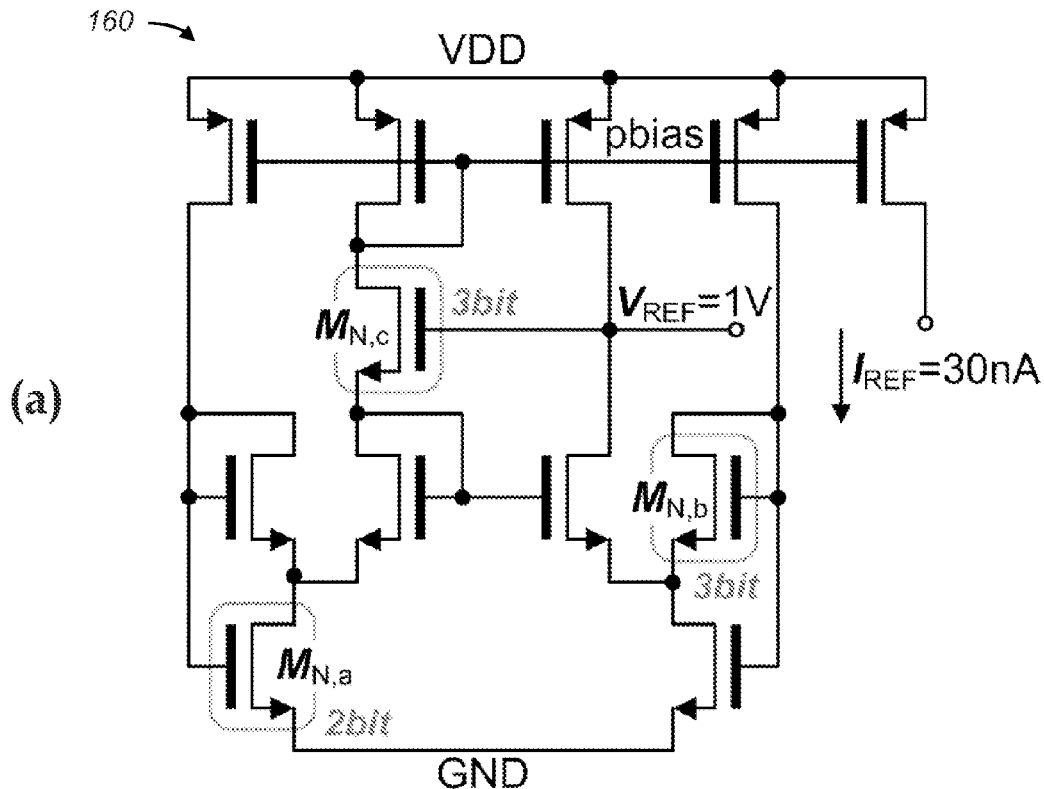
(a)
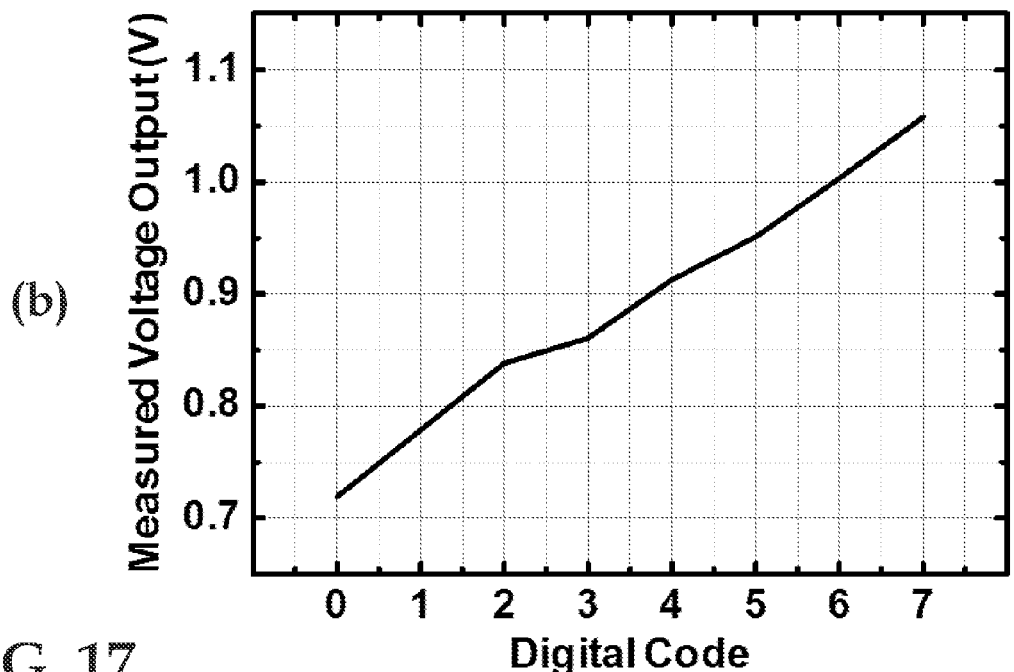
(b)
FIG. 17

| ASIC | | | SAR ADC (per Channel) | |
|---|---|---|---|---|
| Technology | 0.25μm 1P5M CMOS | | Power Consumption | 87.41 nW |
| Total Active Area | 3.2mm x 0.9mm | | Max Sampling Frequency | 31.25 kS/s |
| Channel | 16 | | SNDR | 45.14 dB |
| Preamplifier (per Channel) | | | ENOB | 7.2 bit |
| Supply Voltage | 1V | | INL | 0.3/-0.5 LSB |
| Power Consumption | 0.5 μW | | DNL | 0.70/-0.75 LSB |
| Mid-band Gain | 37.5 dB | | FOM | 20.1 fJ/c-s |
| Input Referred Noise | 4.26 μVrms (1~500Hz) / 5.62 μVrms (10Hz~10kHz) | | Active Area | 180 μm x 220 μm |
| | | | Intra-Skin Communication Driver | |
| NEF | 5.2 (1~500Hz) / 1.69 (10Hz~10kHz) | | Power Consumption | 160 μW |
| CMRR / PSRR | 35 dB / 48 dB | | Data Bandwidth | 320 kb/s |
| Active Area | 180 μm x 500 μm | | Channel Attenuation | -17 dB (1cm) |
| PGA, BPF (per Channel) | | | Energy bit | 500 pJ/bit |
| | | | Voltage/Current Reference Generator | |
| Power Consumption | 50nW ~ 2μW | | Input Voltage | 1.5V ~ 3.5V |
| Programmable Gain | 1,2,5,10 V/V | | Output Voltage | -1.0V: 0.71V ~ 1.05V / -0.5V: 0.35V ~ 0.53 V |
| Active Area | 180 μm x 140 μm | | | |
| High-Pass Corner | 0.5Hz (Tunable) | | | |
| Low-Pass Corner | 18 kHz (Tunable) | | Output Current | 22 ~ 32 nA |

DISTRIBUTED, MINIMALLY-INVASIVE NEURAL INTERFACE FOR WIRELESS EPIDURAL RECORDING

STATEMENT OF FEDERALLY-SPONSORED RESEARCH

This invention was made with government support under ECCS0925441 awarded by the National Science Foundation. The government has certain rights to this invention.

TECHNICAL FIELD

This invention relates generally to medical instrumentation for neural recording and stimulation and, more particularly, to implantable neural interfaces.

BACKGROUND OF THE INVENTION

Recently, the neural activities have been investigated to understand the relationship between the neurons and the mental and physical activities. In order to diagnose disease, such as Parkinson's disease, or to establish a direct interface between brain and external devices, many neural interface systems have been proposed and implemented. Among many other goals of these systems, the ability to continuously record neural signals from awake-behaving animals and humans has been one of the most important goals in neuroscience and neurophysiology. The development and optimization of MEMS and microfabrication technologies has contributed a major part in developing biocompatible, fully-implantable systems that can record from group of neurons up to a single-neuron recording systems. However, more challenges need to be addressed, especially to target the tissue-electrode interface, brain injury due to head movements in addition to power consumption of stand-alone multi-channel systems. On the other hand, old techniques such as electroencephalogram (EEG) typically do not satisfy the requirements of current neuroscience studies for successful diagnosis and treatment of central nervous system (CNS) disorders, neural-based prosthetics, and brain-machine interfaces.

The neural potentials can be categorized by the four primary different signals: single unit action potential (SUAP), local field potentials (LFP), electrocorticogram (ECoG) and scalp electroencephalogram (EEG) according to its sensing locations. All of these methods attempt to record μV-level extracellular potentials generated in the cerebral cortical layers. However, each method varies in its relative invasiveness as well as its spatial and spectral frequency. Generally, there is a trade-off between these parameters; the more invasive the recording technique, the higher the spatial and spectral frequency content of the recorded signal. As the spatial/spectral frequency content increases, so does the amount of information gained from the brain recordings. FIG. 1 depicts a partial cross-section of the head 30 showing the various layers at which different recording approaches are used. The outer layer 32 is the skin where scalp EEG measurements are made. Below that is the skull 34 followed by meninges 36, including the dura mater where epidural recordings are taken. Under the dura mater, ECoG measurements are taken at the surface of the cortex 38. Finally, LFP and Single Unit (Spike) recordings are made within the cortex 38.

A single unit action potential provides the most precise neural activity information. The signal is recorded from single neuron under the cortex, and could provide the 0.2 mm spatial resolution with up to 10 kHz in bandwidth, and 1 mV in amplitude. However, in order to reach the single neuron using micro-machined electrodes, the system is totally invasive and easily infects neural tissues. On the other hand, the scalp EEG potential is obtained on the surface of the scalp. Even though the scalp EEG system, a so-called non-invasive system, is the safest system due to non-penetration of the cranium, the bio-information with which the EEG system could provide is very limited in time and space because the scalp EEG system can only detect the ensemble activities of a number of neurons. Furthermore, in the EEG system, the chronic monitoring in free movement is limited by many external cables and devices. In the last few years, ECoG has gained popularity among researchers as the most pragmatic method for long-term chronic brain monitoring. ECoG system records the brain activities on the surface of the cortex penetrating the meninges which is the brain protection membranes under the cranium: the dura mater, the arachnoid mater, and the pia mater. The ECoG system is less invasive than the action potential system, and can provide better accuracy of bio-information than the surface EEG signal with 5 mm in spatial resolution, 500 μV in amplitude, and up to 250 Hz in bandwidth. However, in spite of these advantages, this system still has some limitations such as large system volume and safety issues because currently a passive electrode array is implanted by opening a 2 cm hole in skull by craniotomy and tethered with a bundle of wires for data transmission.

Intercranial neural interfaces are known, see U.S. Pat. No. 7,548,775, as well as cranial lead anchoring systems that use a threaded attachment within a skull burr hole, see, for example, U.S. Pat. Nos. 7,302,298 and 6,210,417.

Recent progress in CMOS and MEMS technologies has enabled the development of sensor-based mixed-signal circuits and self-powered microsystems such as sensor networks, portable devices, and implantable systems for improving health care. For implantable microsystems powered or recharged by inductively-coupled link, generation of supply-independent voltage/current references can be important. Previous approaches using subthreshold MOSFETs can be complicated, may consume a large area, and may not be optimized for implantable microsystems. Also, these energy-constrained mixed-signal systems, especially for implantable devices, may utilize an analog to digital converter (ADC) that provides low supply-voltage operation (<1V) with a moderate conversion speed (few tens of kS/s) and resolution of, for example, 8 bits. Typically, these devices have used relatively larger feature sizes (>0.25 μm) in order to achieve better 1/f noise performance of a preamplifier; thus, lowering the supply voltage below the threshold voltage (~0.5V) is challenging. Recently, ADCs have been realized in smaller feature sizes (<90 nm) to operate at less than 0.5V. However, applying a large voltage to sampling transistors for rail-to-rail operation may induce potential reliability problems and may require a large area.

SUMMARY OF THE INVENTION

In accordance with one embodiment, there is provided a neural interface, comprising: a housing that includes a threaded body extending from an enlarged head having a tool-engageable surface for threading the housing into and out of a cranial bore; an electrode located at a free end of the threaded body; an electronic circuit at least partially located within the enlarged head, wherein the electrode is electrically coupled to the circuit, and wherein the circuit is configured to wirelessly transmit data received via the electrode.

In accordance with another embodiment, there is provided an epidural recording system comprising a plurality of the neural interfaces. In some embodiments, the neural interfaces can be clustered around or near a central neural interface that receives measured data from the peripheral neural interfaces and transmits that data to an external system. The central neural interface may operate solely to relay data to the external system, or to receive control signals and relay them to the other neural interfaces, and can optionally include an electrode and measurement circuitry to measure neural activity itself.

In accordance with another embodiment, there is provided an analog to digital converter (ADC) that can be used in the neural interface or for other applications. The ADC comprises: a successive approximation register (SAR) having an n-bit binary output; a capacitor array connected to receive some of the bits of the binary output, wherein the capacitor array has an analog output indicative of the charge stored by capacitors of that array; and a comparator including an output connected to the SAR and including a pair of inputs, one of which is connected to the analog output of the capacitor array and the other of which is connected to an adjustable reference voltage.

BRIEF DESCRIPTION OF THE DRAWINGS

Preferred exemplary embodiments of the invention will hereinafter be described in conjunction with the appended drawings, wherein like designations denote like elements, and wherein:

FIG. 6 depicts transcutaneous power transmission that can be used to provide operating power or battery recharging to the neural interface;

FIGS. 7A-7D are diagrams depicting one approach for mechanical packaging of the componentry of the neural interface;

FIGS. 8A-8C are diagrams of a second approach for mechanical packaging of the componentry of the neural interface;

FIG. 9 is a diagram of the main electrical components of the neural interface of FIG. 8;

FIGS. 10A and 10B show exploded and assembled views of individual components of a prototyped implementation of the neural interface of FIG. 8;

FIGS. 11A and 11B show details of the epidural electrode used in the neural interface of FIG. 8;

FIG. 21 is a performance summary of a prototyped implementation of the circuit of FIG. 16 as it was implemented on an ASIC;

DETAILED DESCRIPTION OF THE PREFERRED EMBODIMENTS

Described below are exemplary embodiments of a neural activity recording system constructed in accordance with the invention using neural interfaces that can be used, not just for an epidural recording system, for example, but also for various other tissue-to-electronics applications, including both monitoring and stimulation/control of brain and other tissue. The illustrated neural interface is referred to herein as a BioBolt or MasterBolt depending on the particular type of neural interface being discussed. However, it will be appreciated by those skilled in the art that the neural interfaces can be implemented in a variety of other ways based on the teachings provided herein.

Also described below in connection with the neural interfaces are various electronic circuits that can advantageously be used to provide multi-channel A/D conversion and wireless communication between the BioBolt and other devices such as a MasterBolt, other BioBolts, or other electronics.

Figure 1:
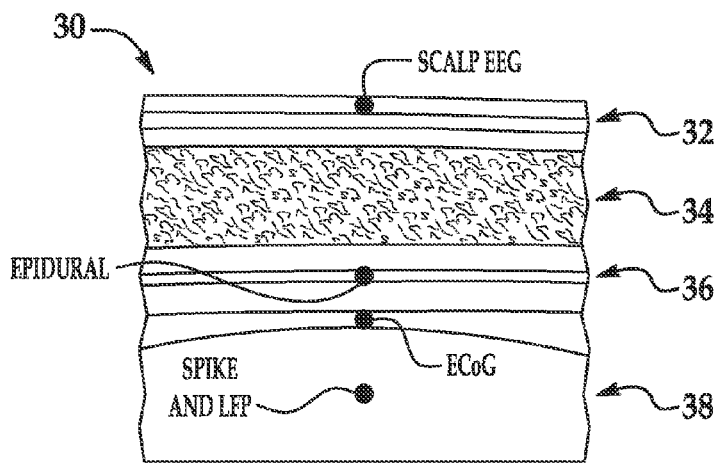
FIG. 1 depicts a partial cross-section of the head showing a comparison of penetration locations of various neural interface systems.
Figure 2A:
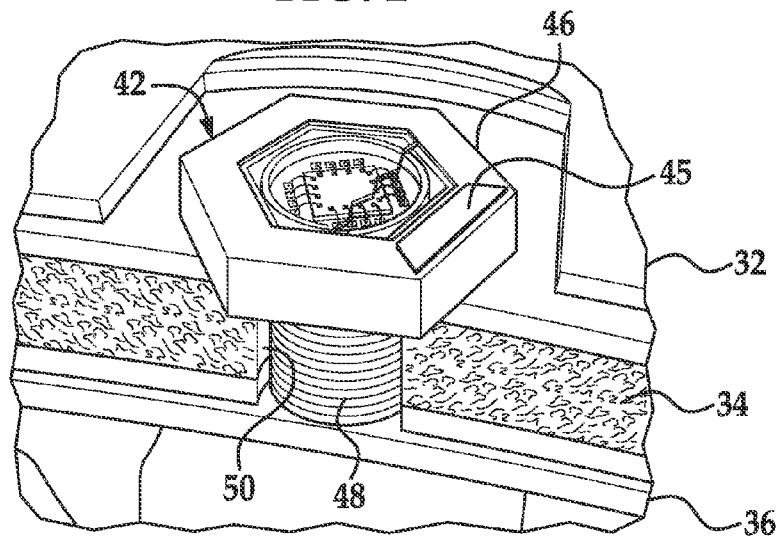
FIGS. 2A and 2B together comprise FIG. 2 which includes perspective views of two parts of an epidural recording system constructed in accordance with the invention.
Figure 2B:
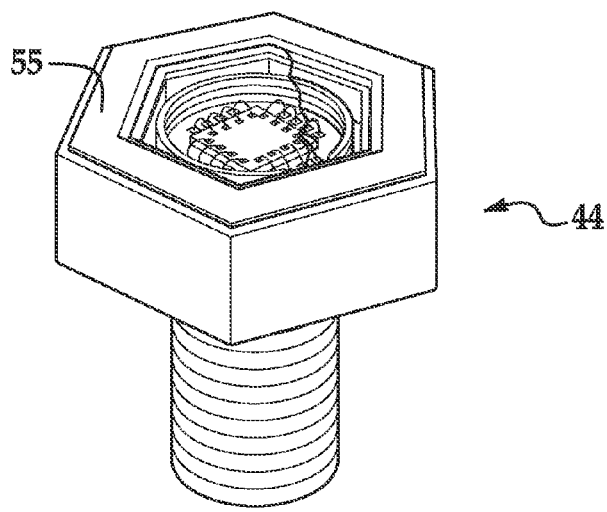

FIGS. 2A and 2B together depict the two parts of a first embodiment of an epidural recording system 40 (also referred to as a neural interface system) that includes one or more BioBolts 42 and a MasterBolt 44. As shown, each BioBolt 42 may be implemented as a hexagonal head 46 and threaded shank or body 48, with the bolt head 46 providing a tool-engaging surface that permits the shank 48 to be threaded into a bore 50 in the cranium 34. The bolt head 46 and shank 48 are at least partially hollowed out to permit insertion of the electronic components of the system that are described below. The axial length of the shank 48 is generally selected such that, when the BioBolt 42 is fully threaded into the skull bore 50 with the bolt head 44 resting against the skull, the free end of the shank engages, but does not penetrate the meninges 36. This can be helpful in dramatically reducing the chance of infection. As will be discussed below, this surface contact of the shank 48 with the meninges 36 permits use of an electrode located on the bottom surface of the free end of the shank, with the electrode engaging the dura mater to record local electrical signals. The MasterBolt 44 can use a similar housing and mounting approach, as indicated in the figures.

Thus, it will be appreciated that the BioBolt 42 may be implemented as a minimally-invasive neural interface for wireless epidural recording or other tissue-to-electronics applications. Epidural field potentials (EFPs) could be an alternative signal solution which measures neural activities on the surface of the meninges 36, especially the dura mater. The epidural microelectrode is close enough to the brain to accurately record high gamma-band activity without actually penetrating the central nervous system. Because the epidural recording method does not penetrate the meninges 36, the risk of infection during surgery and experiment can be reduced substantially. The BioBolt 42 therefore provides a small, fully implantable, epidural microelectrode for chronic long-term recording of cortical activity. The BioBolt 42 enables realization of an efficiently miniaturized wireless epidural recording system that can be embedded inside the skull without craniotomy, and that eliminates any percutaneous connections with external world. This subcutaneous intracranial system feature can provide the BCIs with free movement experiment as well as the safety. As for the wireless signal path, intra-tissue communication method can be utilized to reduce the transmission power and system size. These features and advantages are described further below.

Figure 3:
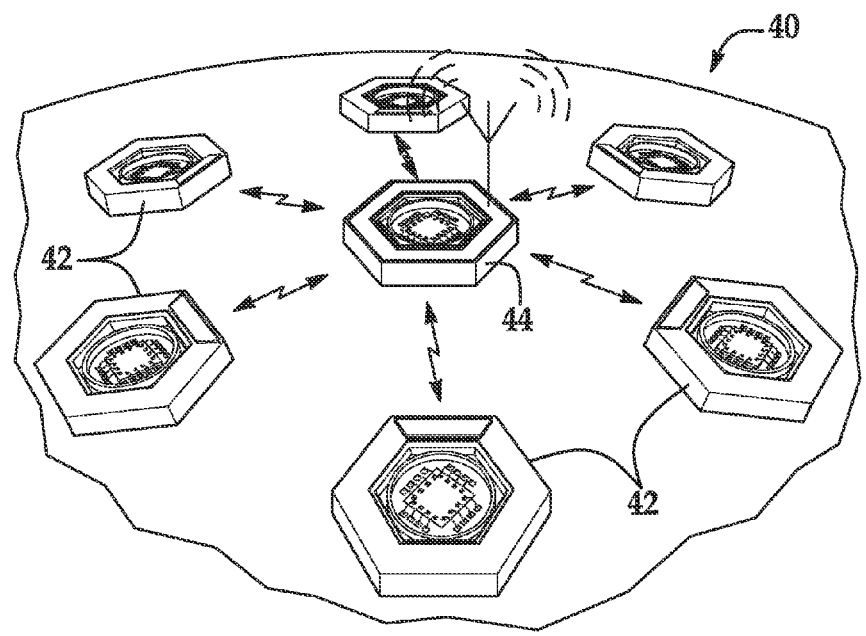
FIG. 3 shows a cluster of neural interfaces of the epidural recording system of FIG. 2 depicting intra-skin communication between neural interfaces and a central, master neural interface that communicates wirelessly with external instrumentation.

Referring now also to FIG. 3, there is shown an embodiment of the epidural recording system 40 that utilizes six BioBolts 42 and a centrally located MasterBolt 44. Together, these components provide a distributed, minimally-invasive neural interface for chronic monitoring of epidural field potentials. Using the BioBolts 42 and MasterBolt 44 with wireless communication between them, this recording system 40 improves the trade-off between the degree of neural information and the invasiveness of subjects to overcome some of the limitations of currently-used chronic neural monitoring systems. Using the cluster arrangement of BioBolts in FIG. 3, spatially distributed BioBolts in the region of interest record the neural activities, specifically epidural field potentials (EFPs) from the surface of dura mater. More or less BioBolts could be used for a particular cluster than is shown. The recorded signals from each BioBolt 42 are transmitted through an intra-skin communication (ISCOM) channel, and collected and transmitted by MasterBolt 44 to an external station (not shown) using FM or other suitable wireless communication. The construction of use of such an external station for recording data received from the MasterBolt 44, or to send control signals to the MasterBolt, is within the level of skill in the art. The bio-compatibility of the recording system 40 can be achieved by choosing Titanium as a frame material coated with bio-compatible Parylene. To secure the long-term reliability for chronic monitoring, the whole system in some embodiments may be subcutaneously implanted inside the cranium and be connected with external devices using wireless telemetry to eliminate any possible infections from external environments. Furthermore, in contrast with other implantable ECoG systems where the operation of the craniotomy is required, the handiness of the bolt-shaped neural interfaces may be used to provide a simple and safe operation protocol of implantation. This feature not only simplifies the implantation procedure but also relieves the constraints in the actual experiment of the subject because the subject can be freely monitored without tethered wire for signal transmission. If necessary, each BioBolt 42 and MasterBolt 44 can be easily disjointed after the experiment.

Figure 4:
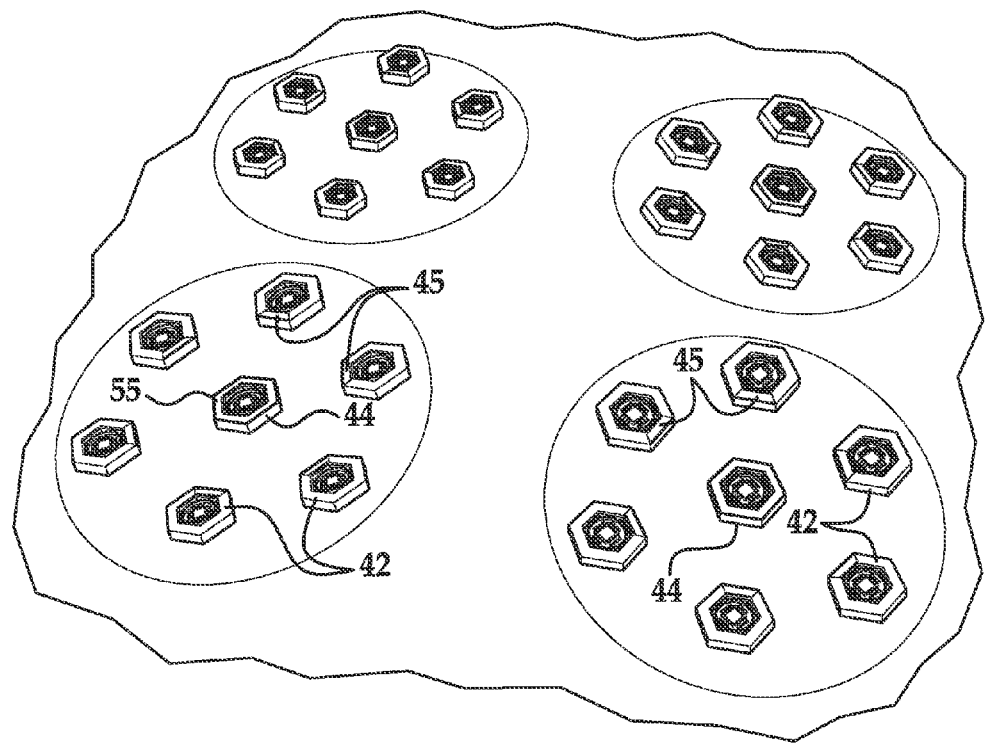
FIG. 4 depicts multiple clusters that can be used for a widely distributed epidural recording system.

To deploy the monitoring sites in a wide area, the neural interface system can utilize a cluster-based operation such as shown in FIG. 4. In each cluster, multiple BioBolts 42 are placed around a MasterBolt 44 which collects the data from the nearby BioBolts and transmits the collected data to external monitoring system. On the demand of wider area coverage, multiple clusters can be deployed.

As will be discussed in greater detail in connection with FIG. 7, each BioBolt 42 is composed generally of three parts: (a) the bolt head 46 with neural processing units, (b) the body or shank 48 with a rechargeable battery inside, and (c) electrodes for epidural recording and intra-skin communication (ISCOM). The neural potential to be monitored is typically low (<100 µV); therefore, it should be amplified and digitized to increase the noise tolerance of the system. To accomplish this, a low-power front-end preamplifier with low noise characteristics is used along with a low-power analog-to-digital converter. For the power-efficient data transmission, the digitized signals may be transmitted through the skin tissue (ISCOM). For supply power, the rechargeable battery will be embedded inside the body of BioBolt 42 and the battery will be recharged through inductive-coupling by transcutaneous power transmission. These features are described below.

Direct wireless data transmission from BioBolts 42 to the external system can provide the flexibility in the deployment of BioBolts in any location. However, this will increase power budget for each BioBolts and may not be the most effective way to use power budget for overall system performance. By properly allocating the functionality to each components based on its power consumption in system perspectives, system performance can be enhanced within a given power budget. This can be implemented using a MasterBolt 44 to collect data from nearby BioBolts 42 so that the wireless power transmission requirements of the BioBolts is much less than if they independently communicated with the external system. For this purpose, the MasterBolt 44 can be dedicated to this function of relaying data, or can itself also perform epidural sensing such that the MasterBolt 44 operates as a BioBolt 42 that has an additional capability of FM telemetry to the external system. The MasterBolt 44 transmits all the collected neural signals from the neighboring BioBolts 42 within a cluster using a single FM channel allocated per each cluster. Techniques for FM and other RF telemetry are known to those skilled in the art. This permits the BioBolts 42 to utilize much lower power transmissions since they need only communicate with a nearby MasterBolt.

As one example and as illustrated in FIG. 3, in case of the multiple nodes operation, to reduce the power consumption for the RF transmitter from each BioBolt, skin tissue can be utilized as a conductive media to transmit the acquired signals from each recording site of each BioBolt to the master node (MasterBolt) using a body area network (or intra-body communication). There are many advantages in using skin as a conductive transmitting media. Some of the technical benefits include: (1) less power consumed compared to RF wireless transmission; (2) less noise and interference; (3) easier implementation and smaller size (no need for antenna or coils required for RF wireless communication).

Figure 5A:
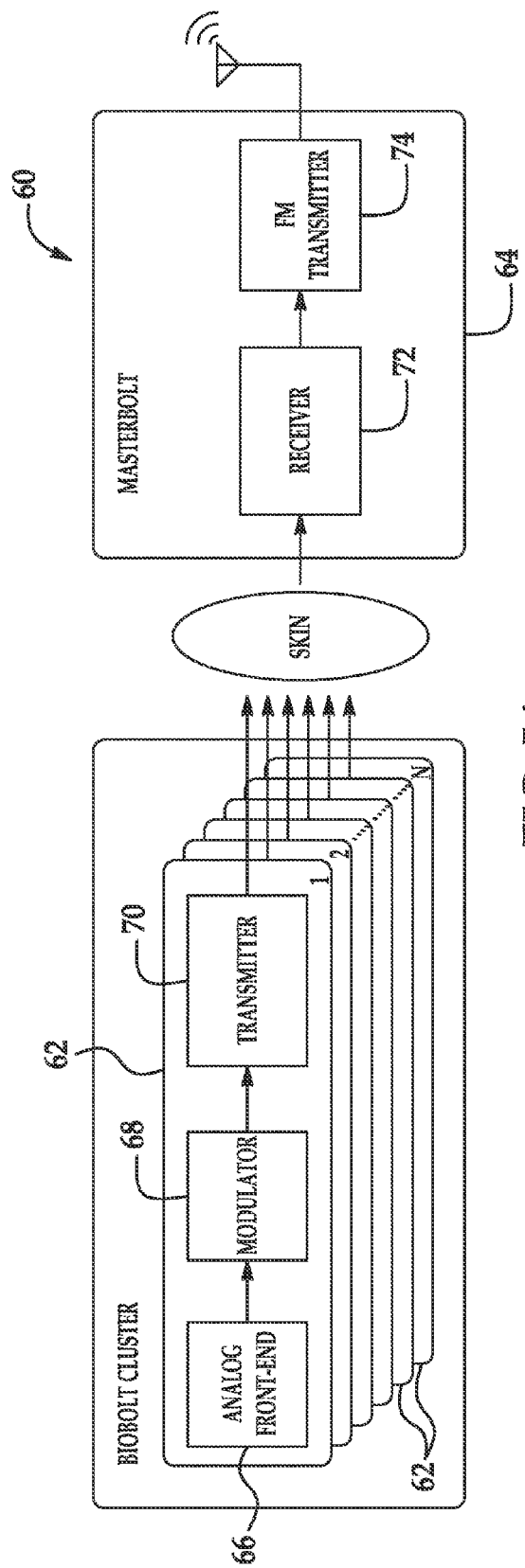
FIGS. 5A and 5B are block diagrams of the electronics used in the neural interfaces of FIG. 2.
Figure 5B:
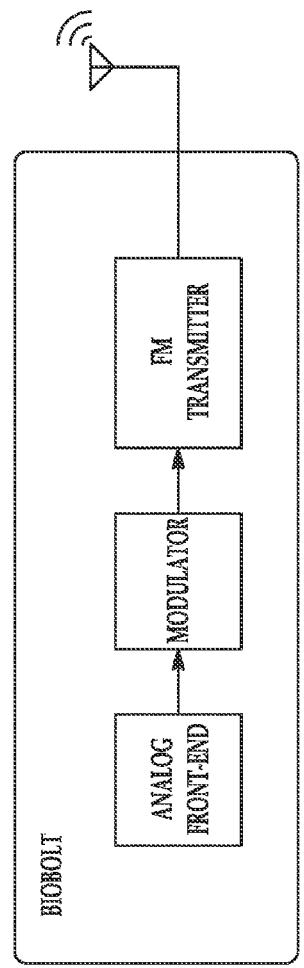

FIG. 5A depicts an overall block diagram of the electronics 60 used in the neural recording system 40. Each BioBolt 42 of a cluster of N BioBolts includes a neural interface circuit 62, each of which communicates via the skin 32 to an aggregating and relaying circuit 64 in the MasterBolt 44. A chemical signal generated by neurons is converted into an electrical signal at the interface between tissue and electrode on the BioBolt 42. Typically, the converted electrical signal is in the range of few hundreds of μV which is relatively weak signal to be processed by the neural signal processor. In order to amplify the weak neural signal precisely and chronically, the neural interface circuit 62 uses an analog front-end circuit 66 that includes an amplifier that is both low-power and low-noise in operation. Circuit 66 can also include a tunable band-pass filter to select the bio-information in the frequency of the interest only. After the analog processing, the amplified neural signals can be converted into the digital domain by analog-to-digital converter for the following signal processes. To address the bandwidth limitation at the wireless data transmission, neural signal compression and/or feature extraction processing unit could also be utilized by circuit 66. BioBolt circuit 62 can be operated in cluster-based or stand-alone modes. In cluster-based operation, the collected, amplified, filtered and converted signals can be compressed by a modulator 68 which may be used to modulate a carrier with the compressed or uncompressed data. This modulated carrier can then be transmitted through the skin via transmitter 70 and collected at the MasterBolt circuit 64 using a receiver 72, and eventually transmitted to the external monitoring system using RF communication 74. In other words, the neural signals are transmitted through hybrid communication channels: intraskin and RF communication for the power optimization. Although not shown in FIG. 5A, as discussed above, the MasterBolt 44 can also operate as a neural interface in the same or different manner as the BioBolts 42, and thus can include the neural interface circuit 62. In addition, the BioBolt 42 can be operated in stand-alone mode. In the stand-alone operation, the modulated (or compressed) signal is transmitted to the external system using RF communication directly from the BioBolt. This is shown in FIG. 5B.

The BioBolts and the MasterBolt can be implanted underneath a layer of skin and can function fully wirelessly. Therefore, no hardwired connection are necessary between the system and the external setup to deliver the required electric power to the system. For this communication, the BioBolts 42 can include an upper, external ISCOM electrode 45 such as shown in FIGS. 2A, 3, and 4, and these can be directionally oriented towards the MasterBolt 44 which includes its own ISCOM electrode 55 that can circle the hexagonal head 46 of the MasterBolt. The electrodes 45 and 55 can be located on the upper surface of the bolt head 46 so that they contact the underside of the skin layer.

In some cases, batteries have been used as the energy source. A disadvantage with this approach is the limited life time of batteries, which does not allow for chronic operation of the system without need for replacing the batteries from time to time. The most commonly used approach to supply electric power to implantable microsystems is inductive telemetry powering. An example is shown in FIG. 6 wherein two coils are mutually coupled together for power transference by inductive coupling between the coils. Thus, a first coil 80 is located on the external side (outside the body) as the primary winding and the other coil 82 on the implant side as the secondary winding. The energy required for the operation of the BioBolt electronics 62 is transferred through this inductive coupling. The receiver coil 82 on the implant side of the inductive link can be wrapped inside the sidewall of the cavity in head 46 of the BioBolt 42. Note that although the bolt head is shown as round in FIG. 6, it can be hexagonal or other suitable shape. Both the BioBolt 42 and the MasterBolt 44 may include these coils, as shown in FIG. 2, and the power received in this manner can be stored, e.g., capacitively for future use, or can be used to recharge an internal rechargeable battery.

The dominant power loss in inductive coupling inside the highly conductive material such as metal bolt frame is due to the eddy current which is generated inside the conductor under the condition of the changing magnetic field. To minimize the eddy current loss in the conductive material, a restrictive magnetic field can be applied by minimizing the diameter of the primary coil to be as large as that of the secondary coil. However, the diameter reduction of the coils will result in a poor coupling as well as misalignment between two coils. To address these issues, a magnetic core such as Permalloy can be used for the secondary coil 82. By placing a permanent magnet inside the primary coil 80, the two coils can be self-aligned to each other. Furthermore, the Permalloy (or whatever high permeability material is used) can be coated on the top of the BioBolt below the receiving coil 82, shielding all the magnetic field from the titanium body. Magnetic flux will be concentrated in the Permalloy because of low magnetic resistance. If the eddy current loss still remains a severe problem, the material for BioBolt metal cast could be replaced by less conductive (or non-conductive) materials such as bio-compatible polymers.

The BioBolt 42 and its electronics 62 and electrodes can be packaged as shown in FIGS. 7A-7D. Titanium (Ti) can be used as a frame material for safety and bio-compatibility of the system. This Ti frame can provide not only a rigid structure for head 46 and shank 48, but can also provide the floating ground and reference for the electronics 62 which can include a fully differential preamplifier packaged inside BioBolts 42 and MasterBolt 44 to suppress any possible DC interferences. To insulate the Ti frame from the rest, the whole system can be coated with bio-compatible insulator, Parylene. The hexagon-shaped head 46 allows for an easy surgical operation during implant or disjoint of BioBolt after experiments, since it can be easily fastened and loosened using conventional tools. Furthermore, the threaded body 48 secures BioBolt to be tightly sealed inside the cranium and increases signal quality by suppressing any possible motion artifacts. Each BioBolt 42 includes a reference electrode 90 located on the bottom of the bolt head 46 and a recording electrode 88 on the bottom surface of the free end of the shank 48 so that it contacts the dura mater. Inside the head 46 of the BioBolt 42, there is a miniaturized platform 84 that can be a printed circuit board (PCB) that holds the fabricated IC 86 (circuit 62) and connects to all other components, such as electrodes 45, 88, and 90, inductive coil 82, and battery 92. The components can be electrically connected to the platform 84 using wire and/or flip-chip bonding. As shown in FIG. 7C, the electrodes and battery can be connected to the miniaturized platform by using flexible cables 94. These interconnections 94 can run along the battery 92 within the center of the BioBolt shank 48 between the electrodes and amplifier circuitry.

Electrodes 88, 45 for epidural recording (Pt) and ISCOM (IrOx), respectively, are isolated from the Ti frame by Parylene. For the secure contact with the dura mater and skin, the recording electrode 88 and ISCOM electrodes 45 are located at the bottom and top of BioBolt 42, respectively. The ISCOM electrode 55 for MasterBolt 44 has a ring shape with a large area to decrease impedance between electrode and skin tissue as well as to receive the neural signals coming from all directions (omni-directional electrode). In contrast, BioBolt has a directional ISCOM electrode 45 in order to suppress any possible interference with other BioBolts from the neighboring clusters. The construction and use of the directional ISCOM electrode is within the skill level of those in the art. The recording electrode 88 is located at the bottom and is connected to the platform in the head by one of the flexible cables 94 through a hole. This hole can be eventually sealed completely after connecting the electrode. The battery can be a rechargeable power source which can be charged via coil 82 from the inductive charging coil 80.

As will be appreciated, many variations and other embodiments are possible. For example, the MasterBolt, if used, need not be a separate cranially-mounted bolt, but could be implemented in other ways, such as by being mounted to the outer skin either near the associated BioBolts or at more remote locations. For example, the relaying function carried out by the MasterBolt (i.e., the receipt of data from the BioBolts and retransmission of that data to an external system) can be done using a wearable, non-invasive device, such as a wrist-mounted (watch) or other external location. This can simplify some aspects of the use of the system, such as by simplifying the process needed to change batteries in the relaying device. The BioBolts can also be packaged in different ways, for example, as a coin so that it can be placed on the cranium or as a pin that can be placed inside the cranium. Also, other electrode structures and means of communicating data externally from the neural interfaces can be used. Moreover, as mentioned above, rather than measuring neural activity, the BioBolts can be used to stimulate neural activity based on control signals generated internally or received from a MasterBolt or external system.

A prototype BioBolt as described above has been implemented to verify the feasibility of the idea. A fabricated BioBolt prototype 100 is shown in FIGS. 8A-8C, which consists of five parts: Ti coated Parylene body 102, Pt electrode 104, battery 106, circuitry 108, and 0.5 mm thick cover 110. All the components were developed individually and integrated inside the body 102 as an implantable prototype system. Each hexagonal side of the head of the bolt body 102 was 8.8 mm in length. The bolt head thickness and shank length were both 5 mm, giving a total of about 10 mm in overall height of the BioBolt 100. The system block diagram for the circuitry 108 of the prototype is shown in FIG. 9. The analog front-ends part (corresponding to circuit 66) included a low-noise preamplifier and analog buffer and was designed and fabricated to optimize the energy and noise performance using 0.25 µm CMOS technology, while the other circuit parts (regulator and FM wireless communication) were implemented using commercially available components on the PCB. In FIGS. 10A and 10B, portions of the fabricated BioBolt prototype 100 are shown. For simplicity, the electrodes are not shown in this figure, but channels to accommodate the electrode interconnects to the circuitry 108 are shown. The top of assembled prototype may be covered with bio-compatible medical graded Silastic to insulate the components from the human body.

Figure 12:
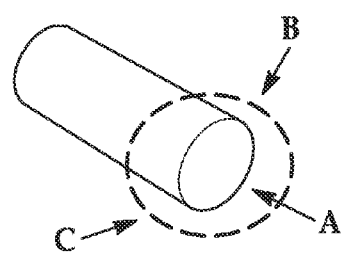
FIGS. 12 and 12A-12C depict additional details of the electrode.
Figure 12A:
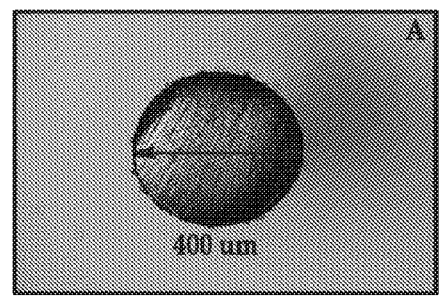
Figure 12B:
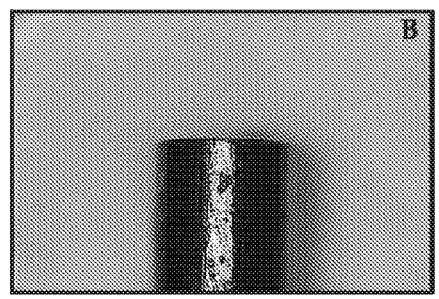
Figure 12C:
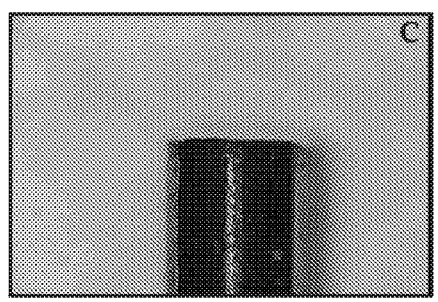

In this prototype 100, the recording electrode 104 is located at the bottom of the BioBolt as shown in FIG. 11A, and may comprise a 400 µm in diameter Pt cylinder surrounded by an outer ring 112 of biocompatible polymer. The cylindrical electrode 104 is shown in FIGS. 11B, 12, and 12A-12C. FIGS. 12A-12C depict views of the cylindrical electrode 104 taken from the viewpoints A-C, respectively, shown in FIG. 12.

Figure 13:
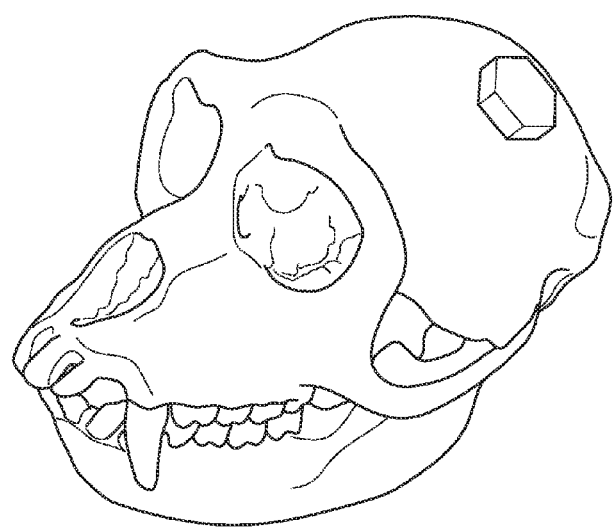
FIG. 13 shows an example placement on a monkey head phantom for the neural interfaces of FIGS. 2 and 8.
Figure 14:
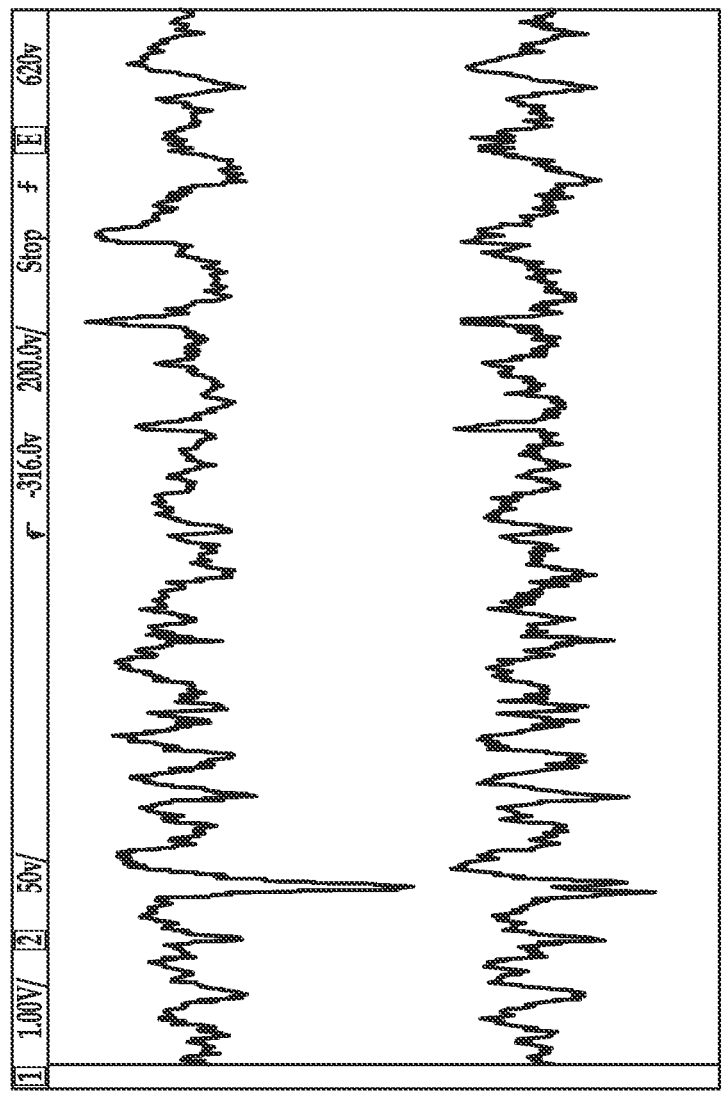
FIG. 14 depicts the results of in-vitro testing of the neural interface of FIG. 8.

The implemented BioBolt prototype 100 can be implanted as shown as a placement example in the monkey head phantom in FIG. 13 for an in-vivo test. An in-vitro experiment has been performed with pre-recorded data. The applied signal was successfully recorded by the fabricated electrode 104 and analog-front end of the circuitry 108 and transmitted through FM telemetry link. This is shown in FIG. 14 which depicts both the applied and retrieved data.

Figure 15:
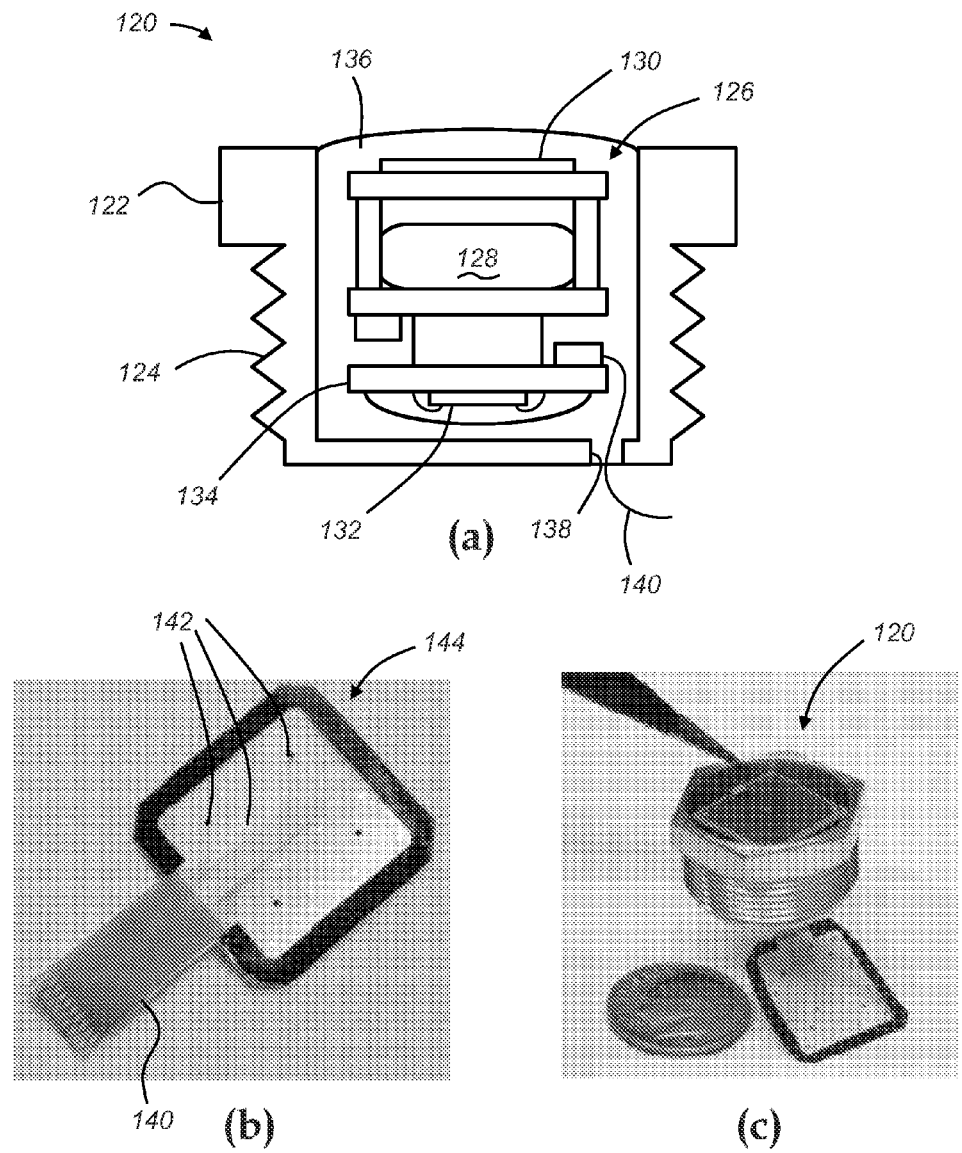
FIGS. 15(a)-(c) show diagrammatic and photographic views of another embodiment of a neural interface constructed in accordance with the invention.

Turning now to FIG. 15(a), there is shown another embodiment of a BioBolt 120 that has a similar construction to the BioBolts 42 and 100 in that it includes a Parylene-coated hexagonal head 122 and shank 124 that are hollowed out to accept the circuitry 126 used to sense neural activity and send it via ISCOM to a MasterBolt. Circuitry 126 includes a rechargeable battery 128, inductor 130, ASIC 132, all of which is mounted on one or more PCBs 134 or other platforms. These components can be sealed in place using Silastic 136. Located at the lower, free end of the shank 124 is a feedthrough hole 138 that permits a ribbon cable 140 or other wiring from the circuit 126 to a set of electrodes 142 that, as shown in FIG. 15(b), are mounted in a spaced configuration on a flexible insulative sheet that can be placed on the dura mater. Thus, rather than having a single electrode mounted at the lower surface of the free end of the shaft, BioBolt 120 uses a separate, flexible microelectrode array 144 that provides N channels of information. Apart from the increased amount of measured information, the shank length can be made somewhat shorter so that the shank itself does not contact the meninges when installed. A prototype of BioBolt 120 was constructed and tested and the assembled prototype is shown in FIG. 15(c).

The flexible microelectrode array 144 has the advantage of minimizing the physical disruption between electrode array and tissues. Rigid structures can be used to insert the flexible electrode array. For example, two metal structures (not shown) may be used to provide a physical support to the flexible electrode array 144 by placing it between the metal structures during the insertion procedure. Also, photolithographically-defined rigid structure may be embedded inside the flexible electrode array 144 for the insertion. After insertion, the rigid part is easily removed from the array. These approaches introduced here are usually utilized to insert the flexible electrode array into the tissue such as single neuron detection or cochlea electrode. However, in ECoG or Epidural EEG system, the electrode array can be placed on the surface of the cortex or dura mater to measure the neural activities. In this case, the spreadable flexible electrode array 144 is folded at the insertion phase to pass through the insertion hole, then, it can be unfolded to cover larger area than the opened hole for insertion procedure.

Figure 16:
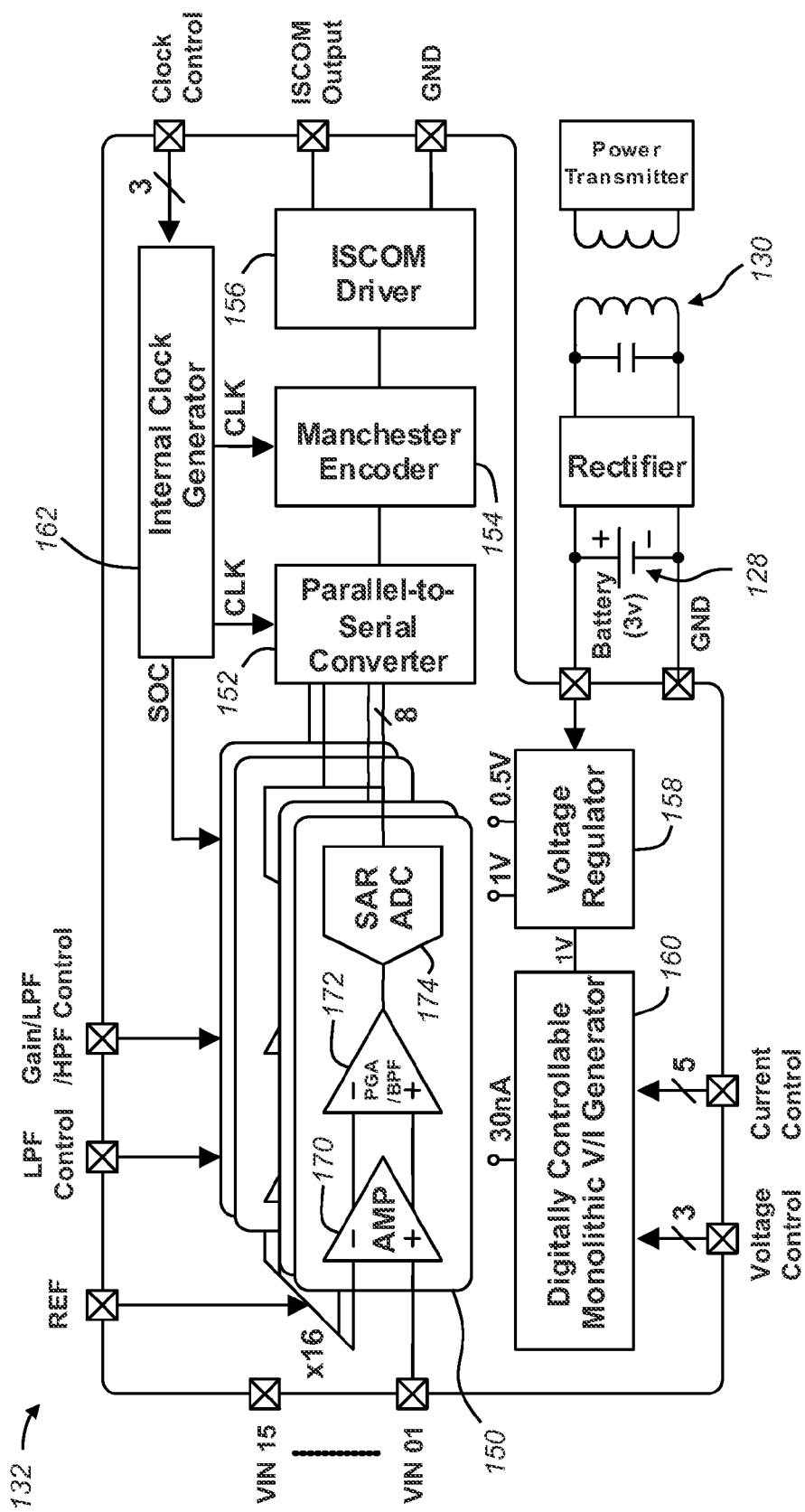
FIG. 16 is a block diagram of circuitry used in the neural interface of FIG. 15(a)

The ASIC 132 used in BioBolt 120 can be implemented as shown in FIG. 16 and, as shown, is designed for use with a sixteen different electrodes, such as may be provided by electrode array 144. The neural activities recorded from the sixteen flexible epidural electrodes 142 are simultaneously amplified and digitized by analog front-end block 150, one for each input channel. The digitized outputs are serialized by a parallel to serial converter 152, Manchester encoded by an encoder 154, and transmitted wirelessly through the skin using an ISCOM current driver 156. For system-level power optimization, all blocks use either 0.5V or 1V supply voltages which are generated by one or more internal regulators 158. A digitally controllable monolithic V/I generator 160 provides a nominal 30 nA and 1V reference outputs which can be used by the various circuits of ASIC 132. These references can be used with current or voltage multipliers to provide the different circuits with the current or voltage required for their operation. Digital blocks are controlled by on-chip clock generator 162. All the blocks inside the ASIC 132 are fully-digitally controllable to accommodate monitoring various neural activities as well as to be tolerable for any possible process variations. Exemplary circuit implementations for many of these functional blocks of ASIC 132 are described below and those that are not can be implemented using circuitry that is within the level of skill in the art.

Figure 17:
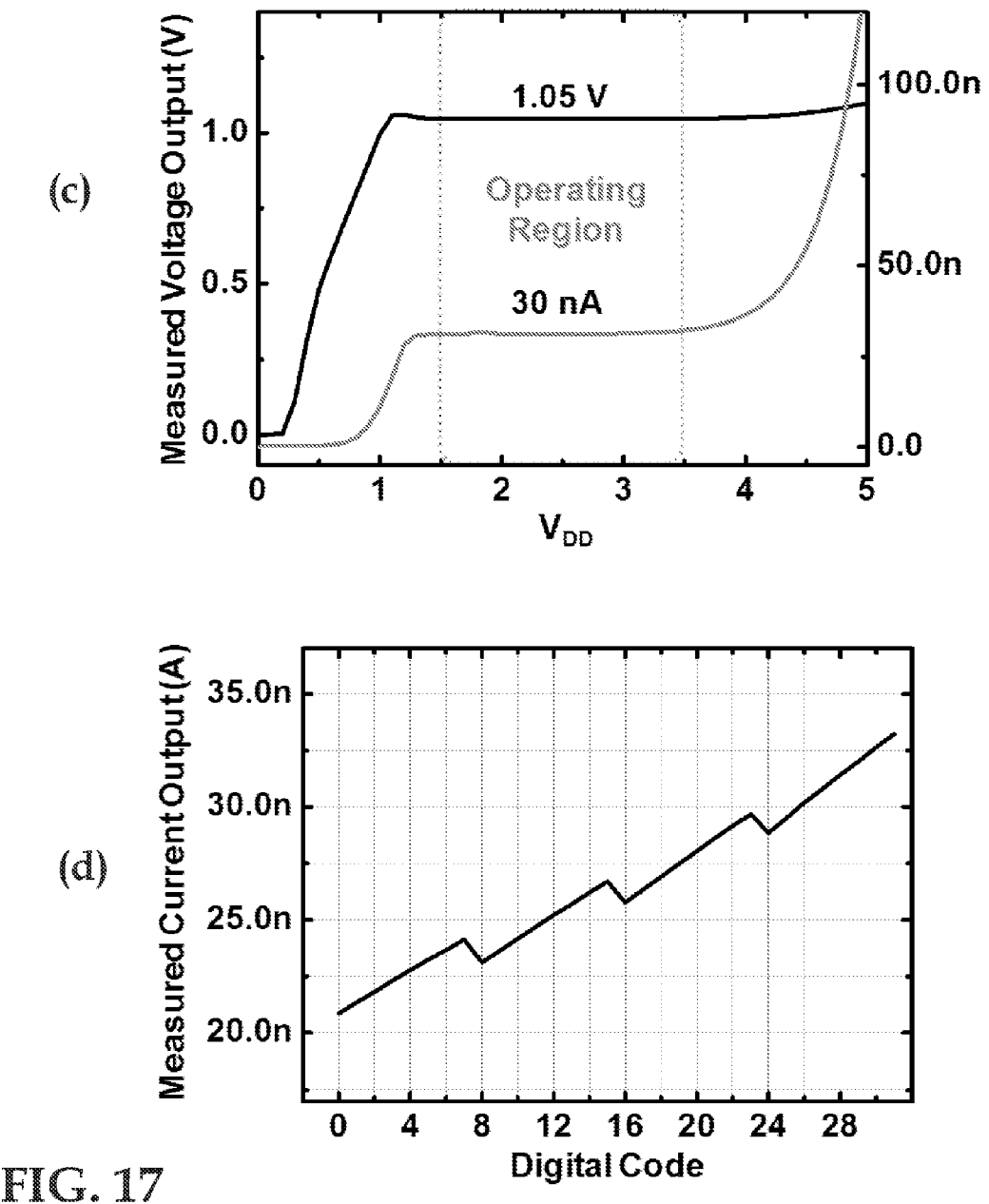
FIG. 17(a) is a circuit schematic of the V/I generator of FIG. 16.
FIG. 17(b) shows the voltage output v. digital codes of the generator of FIG. 17(a)
FIG. 17(c) shows the voltage and current outputs over the $V_{DD}$ supply range for the generator of FIG. 17(a)
FIG. 17(d) shows the current output v. digital codes of the generator of FIG. 17(a)

The digitally controllable monolithic V/I generator 160 was implemented in a small area using the circuit of FIG. 17(a) in 0.25 µm technology and was characterized as shown in FIGS. 17(b)-17(d). The V/I generator 160 was optimized for the implantable BioBolt 120, where temperature dependency is less important, in order to minimize area and provide programmability for the wide range of voltage and current. The circuit design shown does not use a resistor, as is typically required in V/I generators. The measured outputs show that by changing the size of $M_{N,a-b}$ for current and $M_{N,c}$ for voltage, respectively, the regulated V/I output can vary from 0.72V to 1.05V with 8 steps and from 21 nA to 33 nA with 32 steps, respectively. The fabricated V/I generator can operate for input voltages ranging from 1.5V to 3.5V, while consuming only 0.18 µW at 1.5V in an area of 0.011 mm².

Figure 18A:
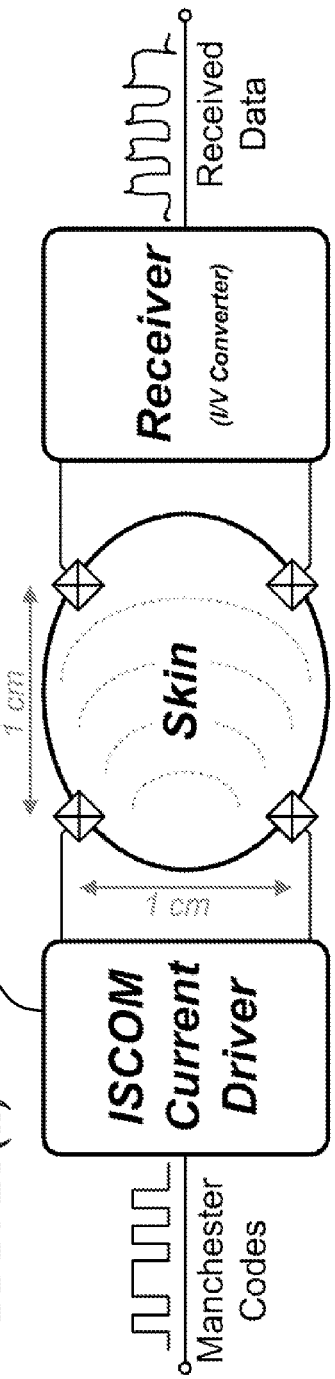
FIG. 18(a) is a block diagram showing the wireless intra-skin communication approach that can be used by the neural interface of FIG. 15(a) to supply measured data to a nearby relaying receiver or other circuit.
Figure 18B:
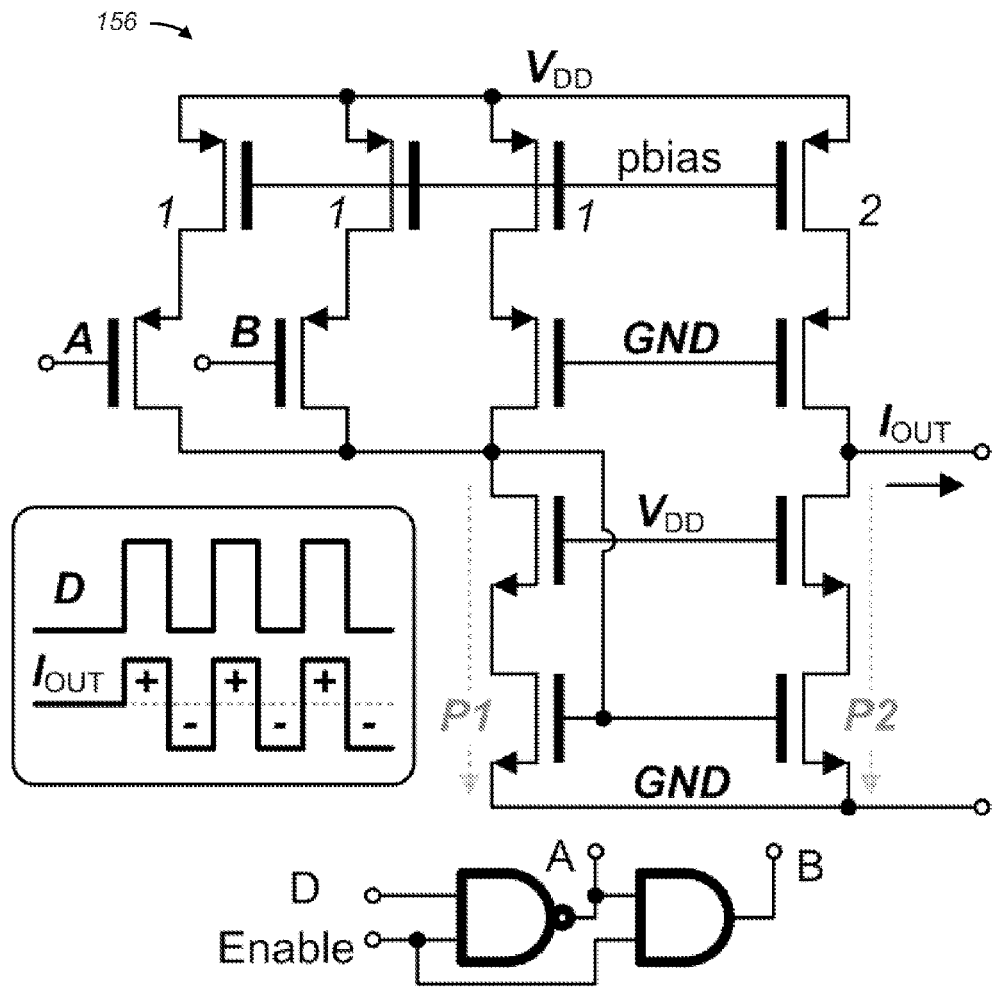
FIG. 18(b) shows a circuit schematic for the ISCOM driver shown in FIGS. 16 and 18(a)
Figure 18C:
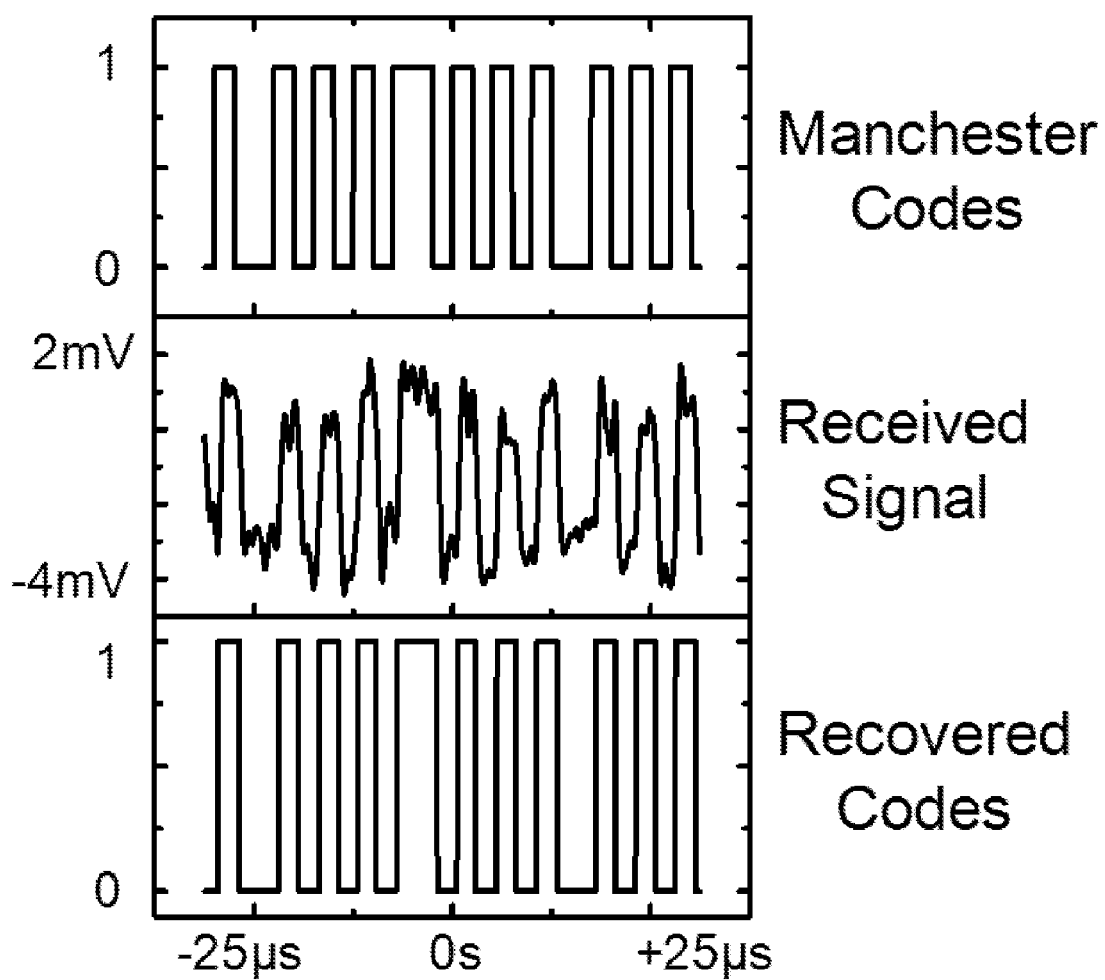
FIG. 18(c) depicts exemplary transmitted, received, and recovered data that can be sent using the ISCOM circuit of FIG. 18(b)

FIG. 18(a) depicts the use of the ISCOM current driver 156 which is used for communication from the BioBolt 120 and which in the illustrated embodiment can utilize electrodes mounted 1cm apart and at a distance also of 1cm from the pickup electrodes of the receiver in the MasterBolt. This data transmission from the BioBolt can be done in a broadcast mode, or using handshaking or two-way communication, as necessary or desirable for a particular application. The intra-skin signal pathway relies on the fact that skin acts as a conductor, and this permits the digitized data to be transmitted at low power consumption (<0.2 mW). One possible issue when current is injected into body is the charge accumulation which should be prevented. One exemplary embodiment of the ISCOM current driver 156 is shown in FIG. 18(b) and is designed to generate alternating current outputs to ensure no charge build-up inside the body. The output current is determined by the current difference between path P1 and P2 according to the modulated signal A and B. An internal control block is designed to generate the signals, A and B, to generate positive current output (Source) at D=1 and negative current (Sink) at D=0 when the channel is enabled, and zero current output when channel is disabled. For measurements, the electrodes are located 1 cm apart from each other as indicated in FIG. 18(a). Manchester codes are transmitted through the skin and received at the receiver side. The sent, received, and restored signals are shown in FIG. 18(c). The transmitted signal does not interfere with neural activities. Using this intra-skin communication technique, a 320 kb/s data bandwidth was obtained at 160 µW (500 pJ/bit) and with a measured channel attenuation of −17 dB.

Figure 19A:
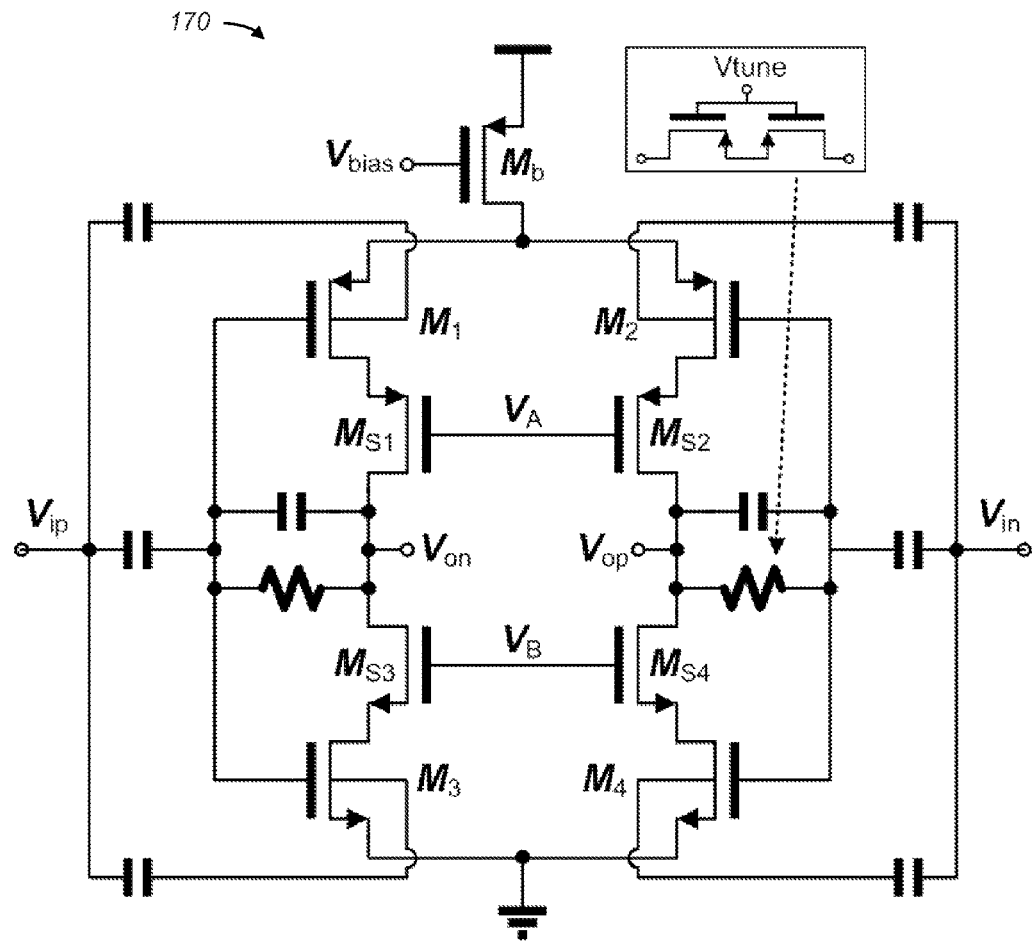
FIG. 19(a) is a schematic circuit of the preamplifier shown in FIG. 16.
Figure 19:
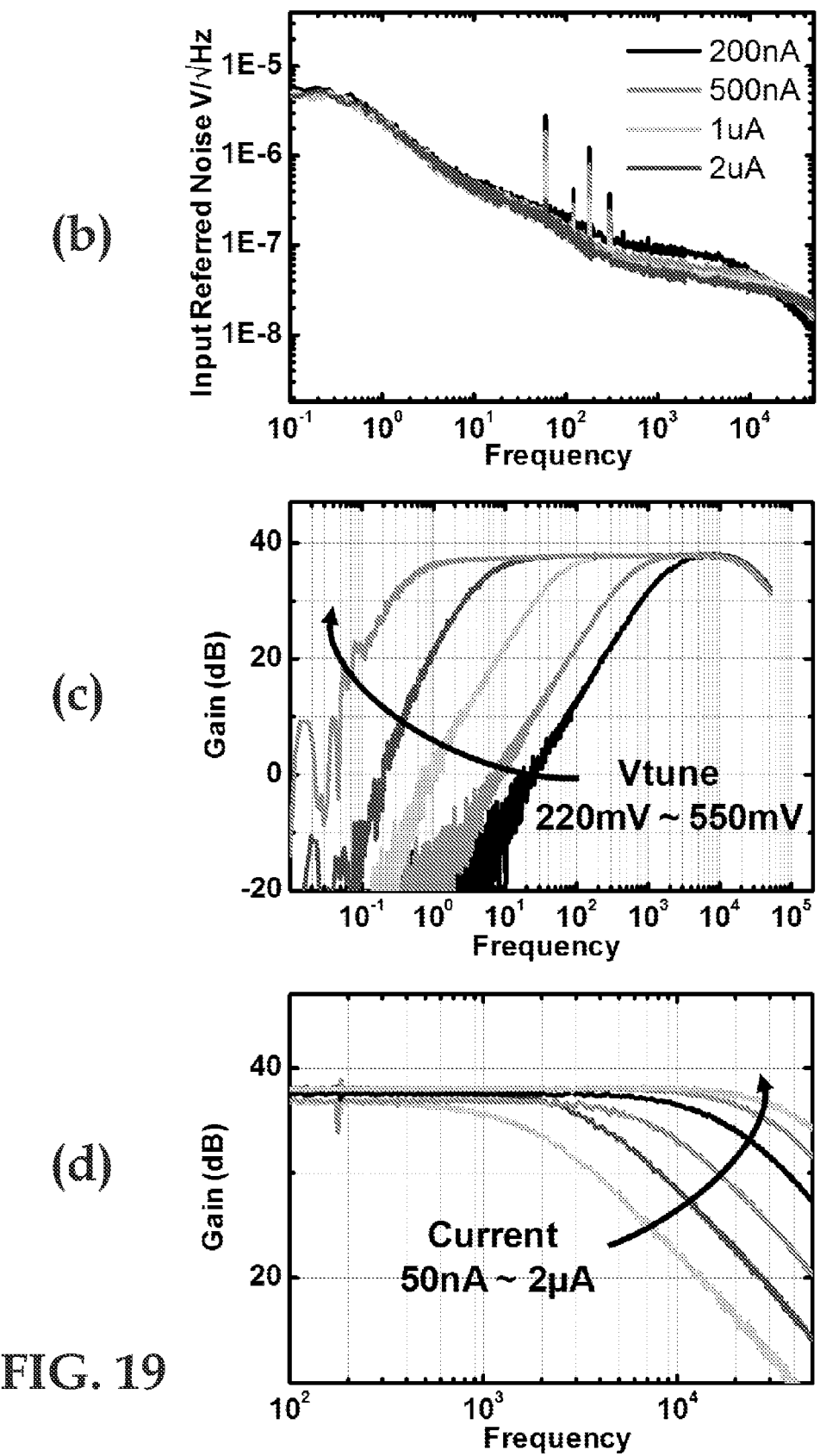
FIGS. 19(b)-(d) show various characterizing data for the preamplifier of FIG. 19(a), including measured input referred noise and frequency responses.

Referring back to FIG. 16, each channel's analog front end block 150 includes a preamplifier 170, programmable gain amplifier 172 with a controllable bandpass filter, and a successive approximation register (SAR) analog to digital controller (ADC) 174. FIG. 19(a) shows one embodiment of the preamplifier 170 using floating body transistors as the input transistors. One way to increase the noise-power efficiency of preamplifiers is maximizing the transconductance for input transistors while minimizing it for the rest of transistors. The illustrated preamplifier is a push-pull topology with floating-body transistors where the body acts as the second gate of transistors to increase the transconductance by 20~30%. The floated body is pseudo-biased by the leakage current generated at the path between source and body. As implemented on the ASIC 132, the preamplifier had, at a bias current of 0.50 µA, a measured mid-band gain, bandwidth, and thermal noise floor of 37.5 dB, 18 kHz, and 47 nV/√Hz, respectively. The measured rms noise was 4.26 µVrms for 1 Hz to 500 Hz (NEF=5.2) and 5.62 µVrms for 10 Hz to 10 kHz (NEF=1.69), respectively. While this topology shows an excellent noise efficiency at high frequencies (>1 kHz) where the thermal noise is dominant, the noise efficiency at low frequencies (<10 Hz) degrades due to 1/f noise. FIG. 19(b) shows measured input referred noise for various bias currents, and FIGS. 19(c) and (d) show frequency responses of the preamplifier 170 with BPF/PGA (at PGA gain=1).

Figure 20A:
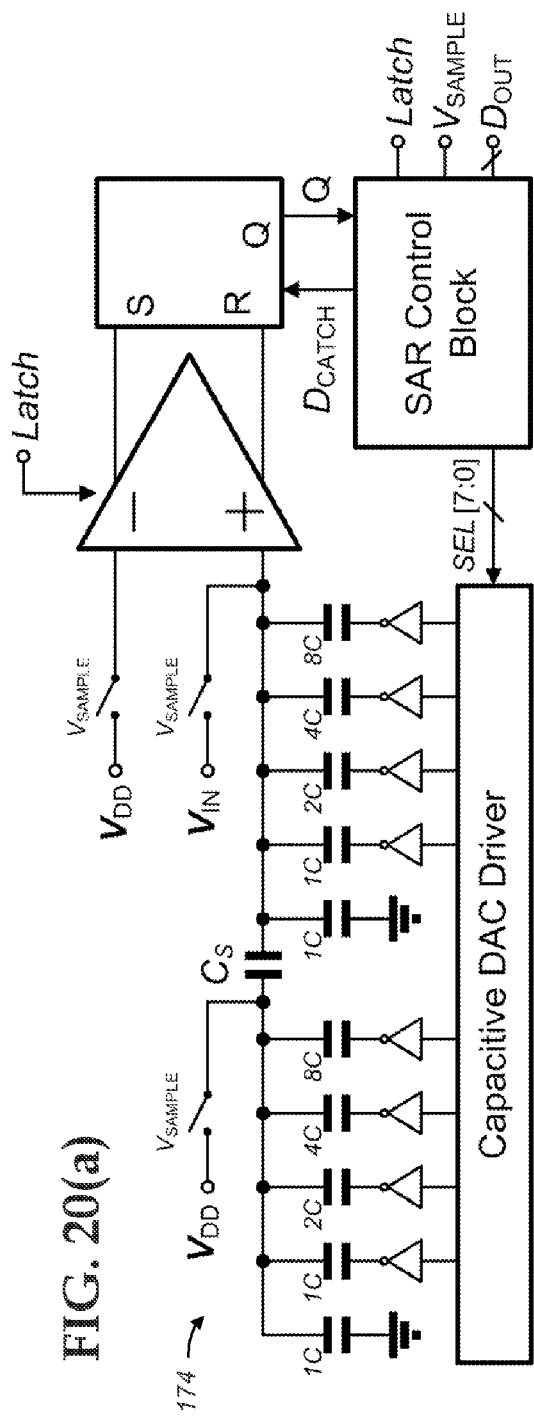
FIG. 20(a) is a block diagram of an SAR ADC that can be used in the circuitry of FIG. 16.

In multi-channel systems, on-chip ADCs are typically embedded with a multiplexer to save the power and area. However, this methodology suffers from a delay caused by the input capacitance of ADC and the on-resistance of multiplexers and the crosstalk between channels. To compensate this, buffers are utilized before and after the multiplexer. To address these issues, the SAR ADC 174 in each channel was implemented in 0.25 µm technology as a rail-to-rail SAR ADC. This is shown in FIG. 20(a) as an 8-bit ADC and its measured INL and DNL are shown in FIG. 20(c). The SAR ADC 174 includes a successive approximation register (SAR) having an n-bit binary output and a capacitor array that receives the binary output bits from the register and develops an analog output indicative of the charge stored by capacitors of that array. Using a known successive approximation algorithm, the ADC iteratively steps its output bits towards a value that produces an analog output of the capacitor array that approximates the sampled input voltage. Once this approximation has converged to the sampled input, the n-bits of data can be output as a digital representation of the input voltage.

Figure 20B:
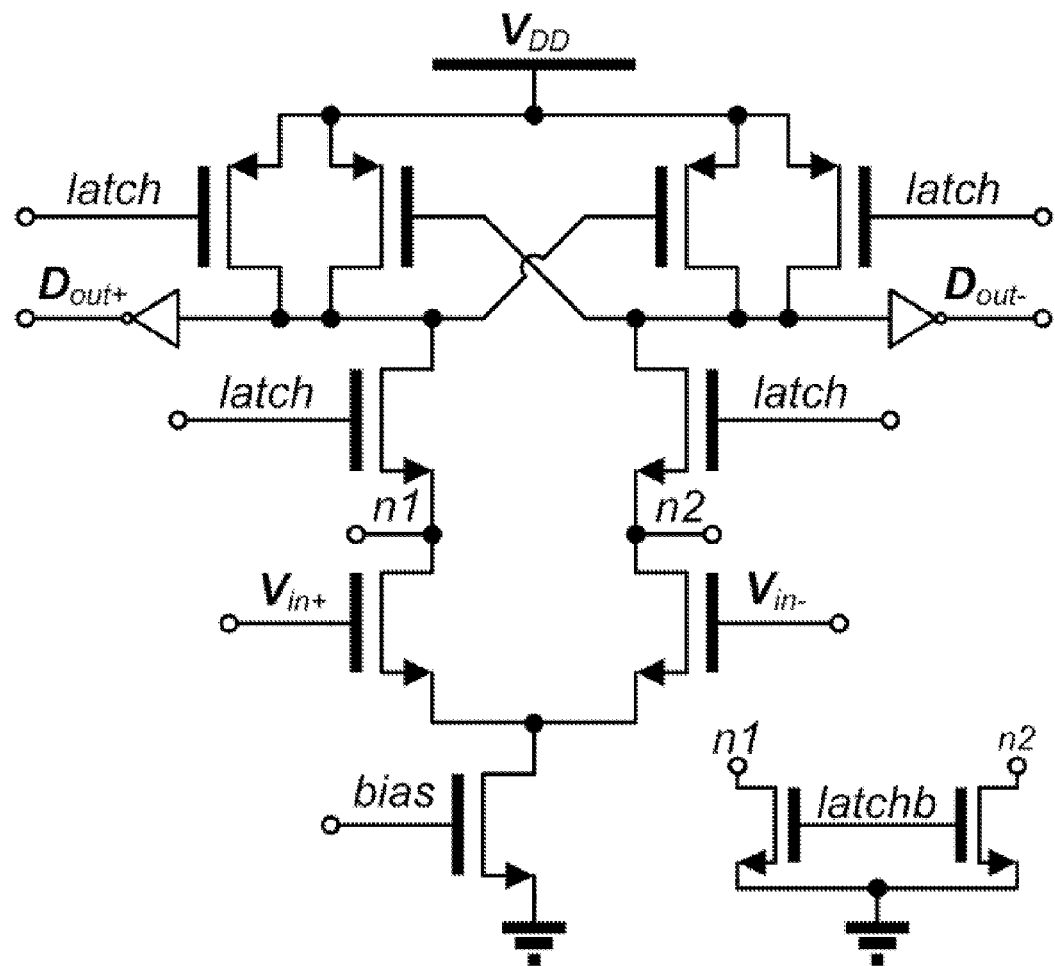
FIG. 20(b) is a schematic of the comparator used in the ADC of FIG. 20(a)
Figure 20C:
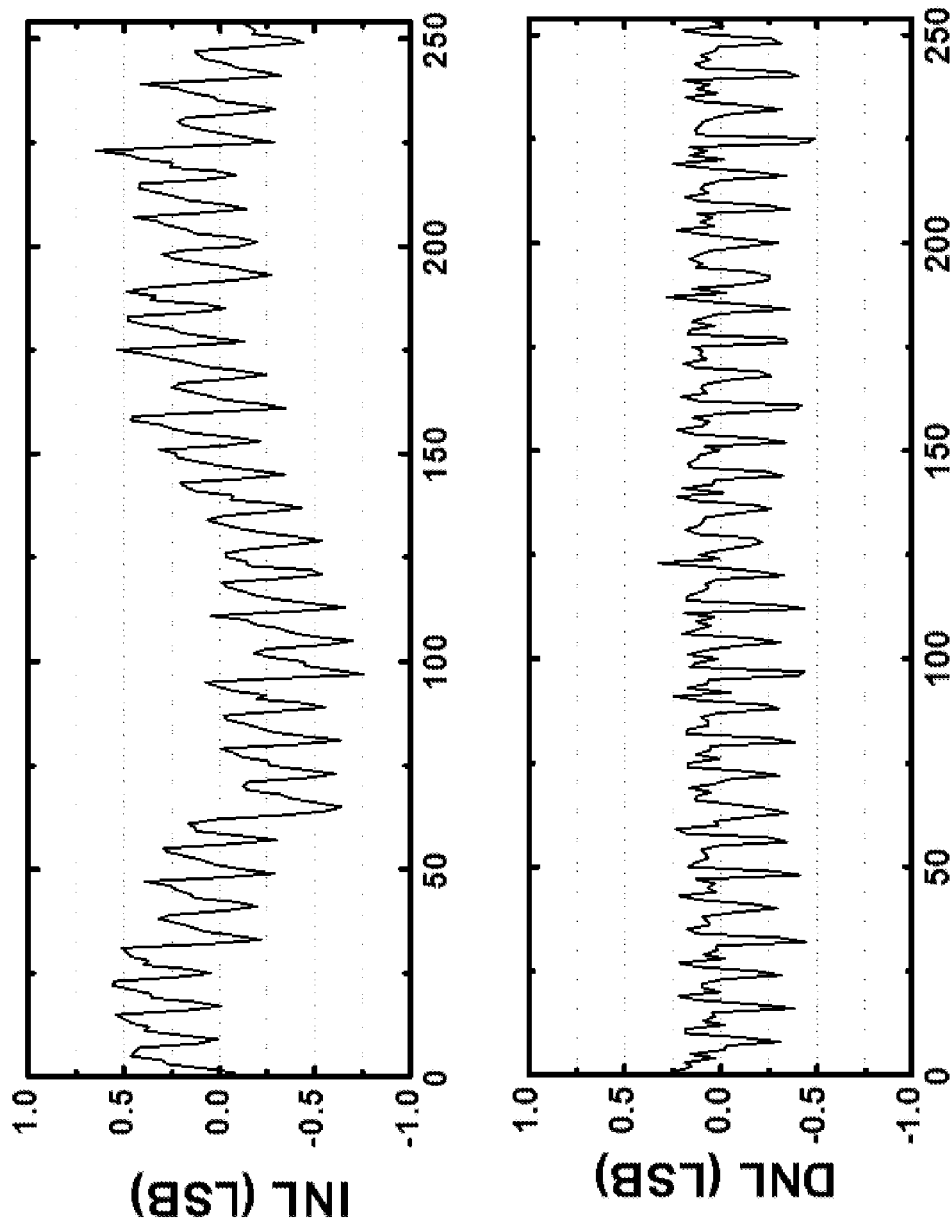
FIG. 20(c) shows graphs of INL/DNL for the comparator of FIG. 20(b)

FIG. 20(b) depicts a circuit design of a digital dynamic regenerative comparator that may be used as the comparator shown in FIG. 20(a) to avoid linearity problems when operating at the low voltages used by ADC 174. In order to minimize conversion hysteresis due to low driving voltage (0.5V) for reset transistors, transmission gates are used. Both n1 and n2 nodes as well as the output nodes ($D_{out+}$, $D_{out-}$) are reset. For simplicity, in the schematic of FIG. 20(b) only the one-type of transistors are shown for the transmission gates. Most of comparator power is consumed during the transient (latch) phase. Therefore, power can be reduced by limiting the transient current. Tail current source is used to limit the transient current at the cost of speed which is less critical in most implantable device applications. The negative input of the comparator is tied to VDD in order to ensure the input transistor operates in near moderate inversion.

The fabricated ADC 174 consumes 87.41 nW (FOM=20.1 fJ/c-s) at 31.25 kS/s with core area of 0.041 mm². For the sixteen channels, the total power and area are 1.4 µW and 0.656 mm², respectively. The sampling frequency of the ADC is digitally controllable and varies from 1 kS/s to 31.25 kS/s. Further operational and construction features of the SAR ADC 174 will be described below in connection with a second SAR ADC that provides both the rail-to-rail operation as well as an over the rail boost mode.

Figure 22:
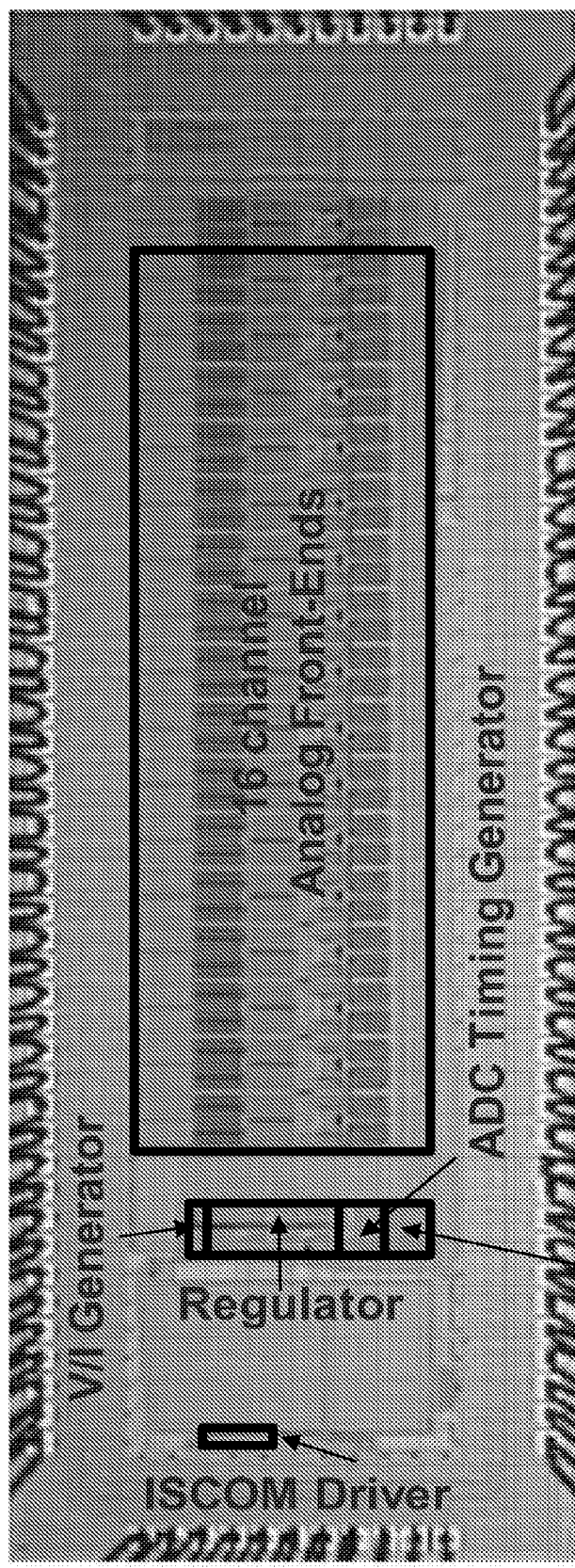
FIG. 22 is a photograph of the prototyped ASIC containing the circuit of FIG. 16.

FIG. 21 shows the performance summary of the ASIC 132 and FIG. 22 shows a microphotograph of the ASIC 132 fabricated using 0.25 µm 1P5M CMOS technology. The core area of the chip is 3200 µm×900 µm, and total power consumption is 365 µW.

Figure 23:
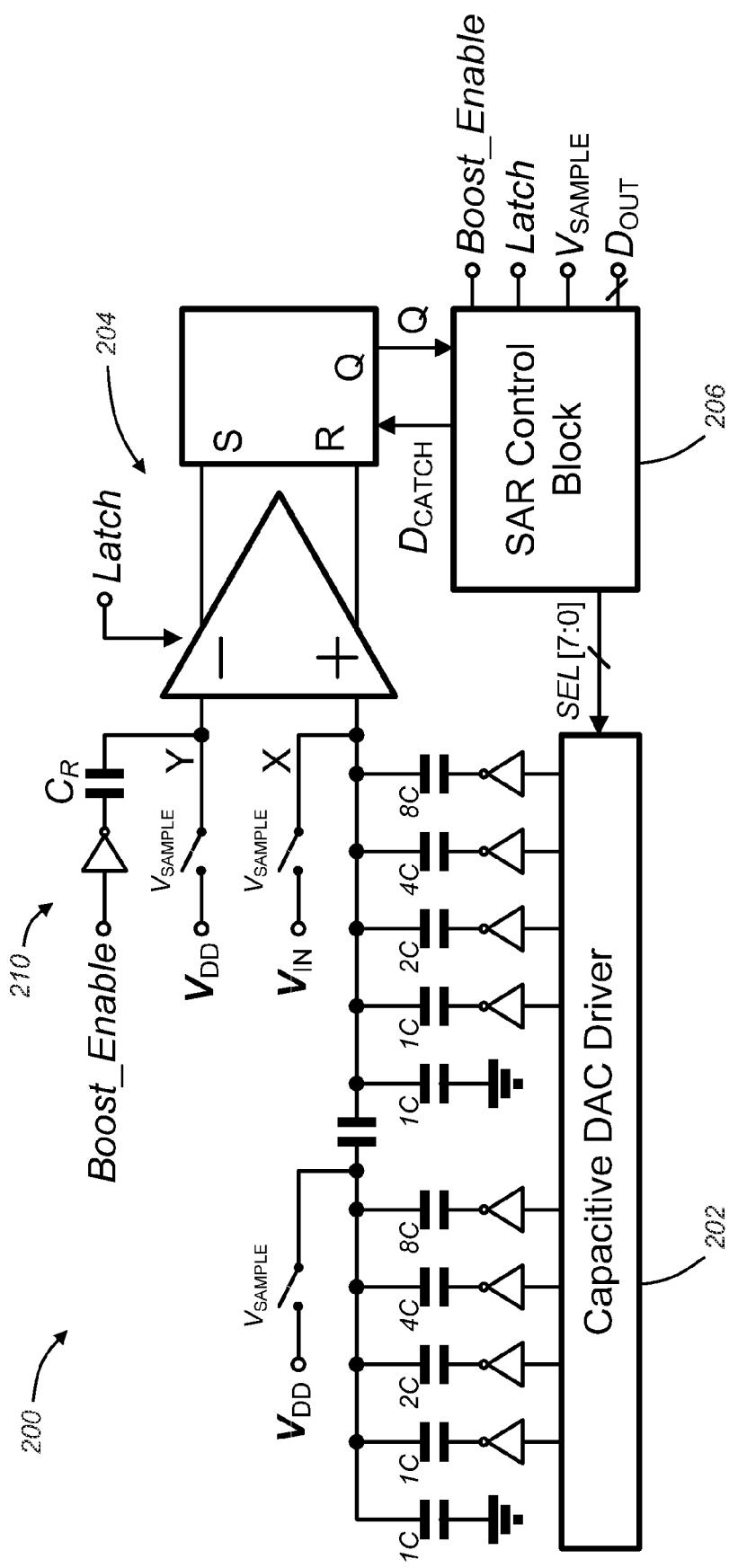
FIG. 23 is a block diagram of another embodiment of an SAR ADC that can be used in the circuit of FIG. 16 or for other applications.

As noted above, some currently existing ADCs have been realized in smaller feature sizes (<90 nm) to operate at less than 0.5V, but that applying a large voltage to sampling transistors for rail-to-rail operation may induce potential reliability problems and may require large area. Also as noted above, the SAR ADC 174 of FIG. 20(a) can be reliably implemented in 0.25 µm technology with low power and in a small chip area. FIG. 23 provides another SAR ADC design that can be used in the BioBolts described above, and can be used in other applications for which a small area, low power ADC operation is necessary, desirable, or otherwise feasible. The SAR ADC 200 of FIG. 23 is similar to that of the ADC 174 of FIG. 20(a), but additionally includes an over-the-rail boost capability using a Boost_Enable signal from the SAR Control Block that boosts the reference voltage up, thereby allowing for an additional bit above the MSB. A prototype of this ADC 200 was fabricated, tested, and characterized, as discussed below.

Figure 25:
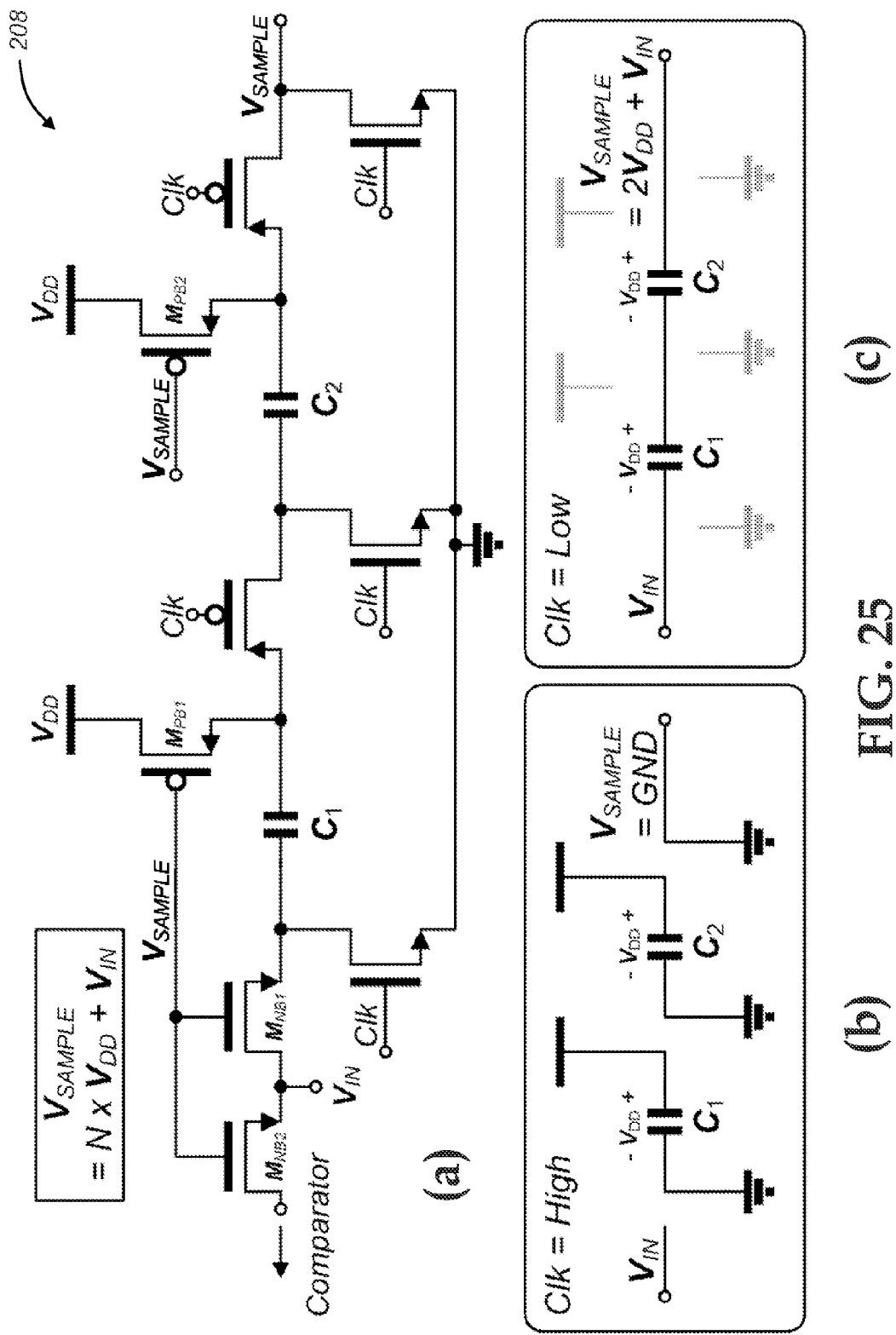
FIG. 25(a) is a circuit schematic of a bootstrapping circuit that can be used in the ADC of FIG. 23.
FIGS. 25(b) and (c) depict the principal of operation of the bootstrapping circuit of FIG. 25(a)
FIG. 25(d) shows conceptual output waveforms for the bootstrapping circuit.

SAR ADC 200 includes an 8-bit split-CDAC 202, comparator 204, SAR control block 206 (which includes an internal clock generator), bootstrap circuit 208 (FIG. 25), and input range booster 210. The input signal is sampled when a bootstrapped $V_{SAMPLE}$ is high. The sampled input signal is compared with the reference voltage ($V_{DD}$) that is sampled into capacitor ($C_R$) identical to the CDAC to compensate any possible leakage and injection of charge at node X during the conversion. As the conversion steps are performed, the potential at node X is approaching to that at node Y. In addition to 0.5V rail-to-rail operation, the capacitor ($C_R$) can be utilized to extend its operation over the rail by boosting the reference voltage up to 2VDD through capacitive coupling. Boost_Enable allows an additional bit above MSB. Thus, this technique enables ADC to digitize the input signal over the rail at the cost of additional power consumption for charging $C_R$ and to effectively operate at 9 bit resolution. Some exemplary specific circuits for the various functional blocks of FIG. 23 are shown in the figures and are described herein. For example, comparator 204 may be implemented using the circuit of FIG. 20(b), and the bootstrap circuit 208 may be implemented as shown in FIG. 25. Other blocks that are not further described or shown may be implemented conventionally using circuits known to those skilled in the art.

Figure 24:
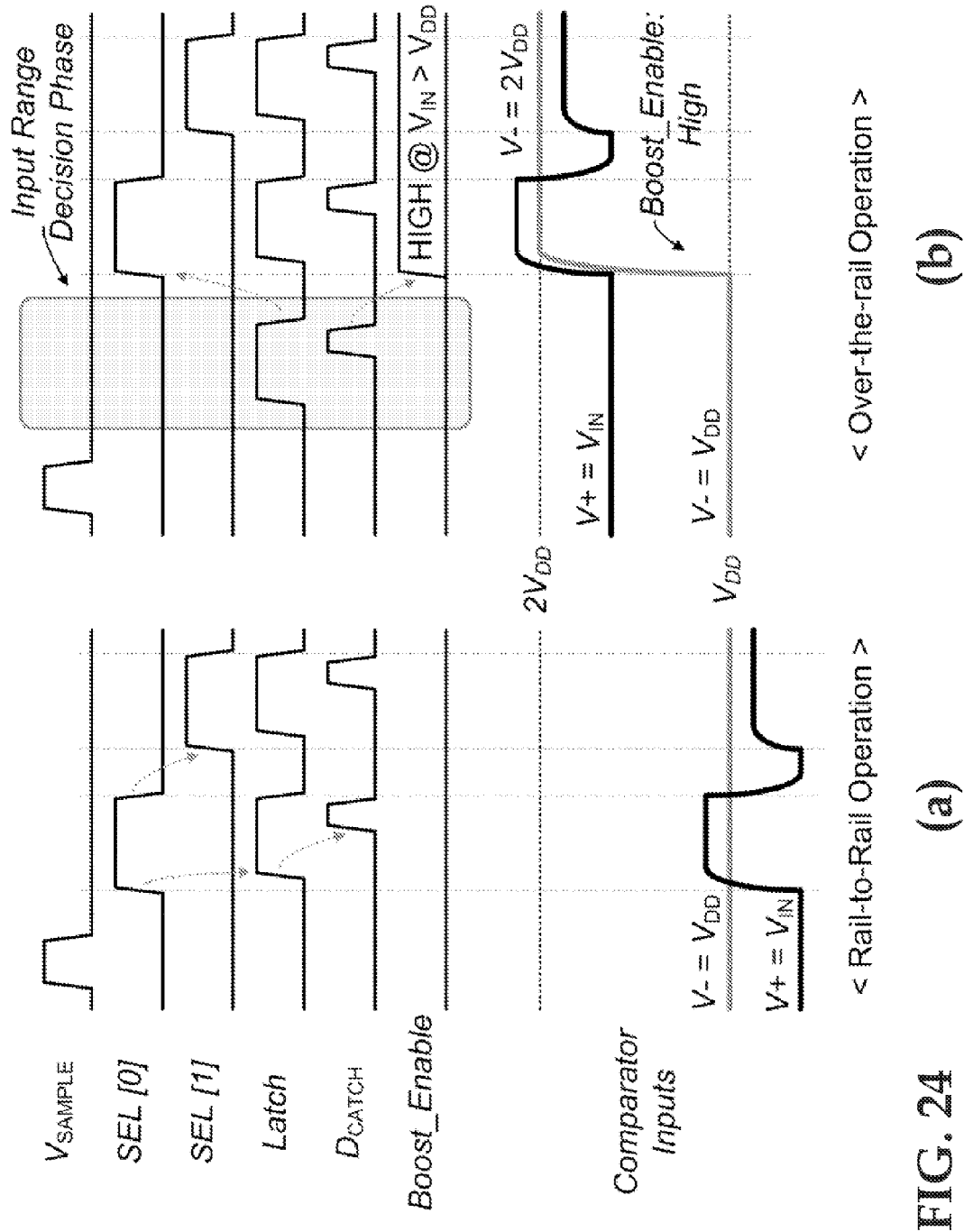
FIGS. 24(a)-(b) depict timing diagrams of the ADC of FIG. 23 operating in rail-to-rail and over-the-rail modes, respectively.

ADC 200 can operate in two modes: (1) rail-to-rail input range in normal operation and (2) over-the-rail range when boosting is turned on. FIGS. 24(a) and (b) show timing diagrams for these two modes, respectively. All the control signals are generated internally using the delay circuit. In order to suppress kick-back effects which can be severe due to the absence of preamplifier, the timing of the latch signals is turned off before the DAC status is updated to minimize differential injected charge amount before and after latching. Both modes of operation compare input signals with the reference signal according to Sel[n] and latch signals. Firstly, the input range is compared with VDD during input range decision phase. If the input signal is below VDD, the following steps are identical to rail-to-rail operation. If the input signal is above VDD, the reference signal is boosted from VDD to 2VDD turning on Boost_Enable. For the rail-to-rail operation, the positive input approaches the reference voltage as the conversion step progresses, as shown in FIG. 24(a). For over-the-rail operations, the input signal approaches to the boosted reference voltage, as shown in FIG. 24(b). It should be noted that the input transistors operate in triode region during the over-the-rail operation; thus the transconductance decreases. The measurement result shows the degradation by 10 dB in SNDR during the over-the-rail operation compared to rail-to-rail operation.

Figure 25D:
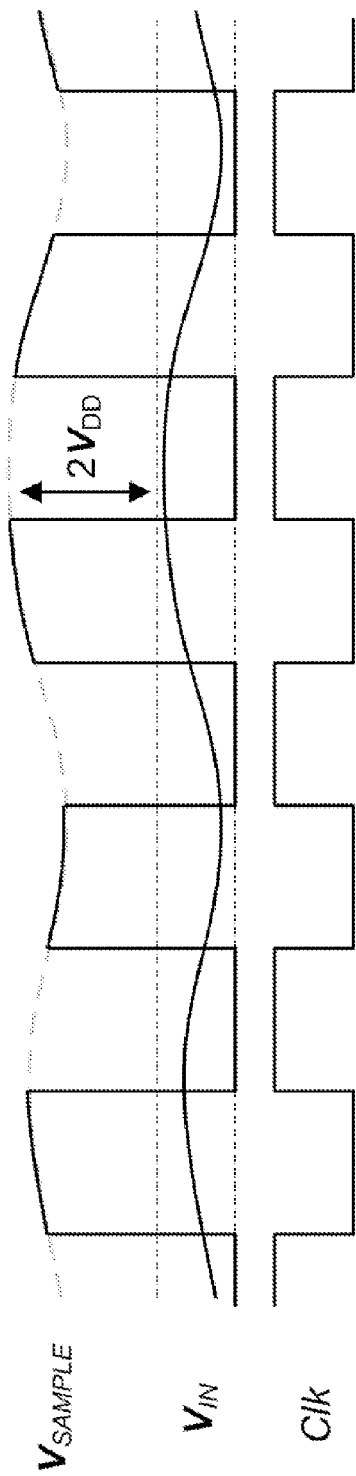

The bootstrapped circuit 208 for sample and hold is shown in FIG. 25(a). The operation of circuit 208 is as follows: when Clk is high, the booster capacitors are charged to $V_{DD}$. This is shown in FIG. 25(b). When Clk becomes low, the capacitors are connected in series to generate a bootstrapped signal by capacitive coupling which can be expressed as $V_{SAMPLE}=N \times V_{DD}+V_{IN}$, where N is the number of voltage doubler stages. This is shown in FIG. 25(c). The conceptual output waveforms are shown in FIG. 25(d). The settling time of $V_{SAMPLE}$ can be within one clock cycle. For proper operation, $M_{PB1,2}$ and $M_{NB1,2}$ should be controlled by the bootstrapped voltage ($V_{SAMPLE}$) and the body of $M_{pB1,2}$ should be connected to the capacitor side as shown in FIG. 25(a). Because of the larger feature size and its high affordable voltage swing (0.25 µm/2.5V), the gate oxide lifetime of these bootstrapped transistors will not degrade, which can otherwise be a serious problem for sub-100 nm technologies.

Figure 28:
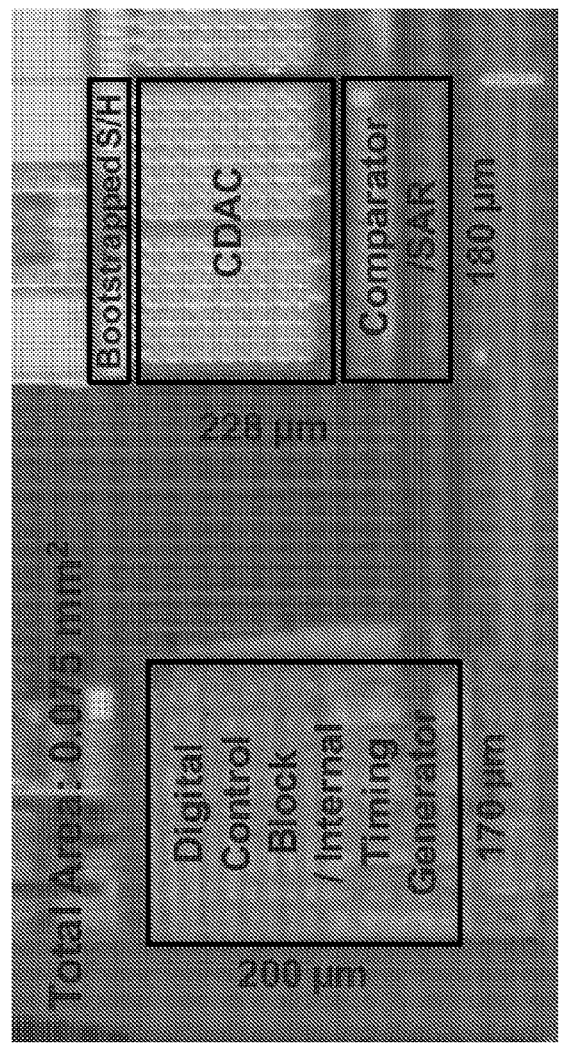
FIG. 28 is a photograph of a prototype of the ADC of FIG. 23.
Figure 26:
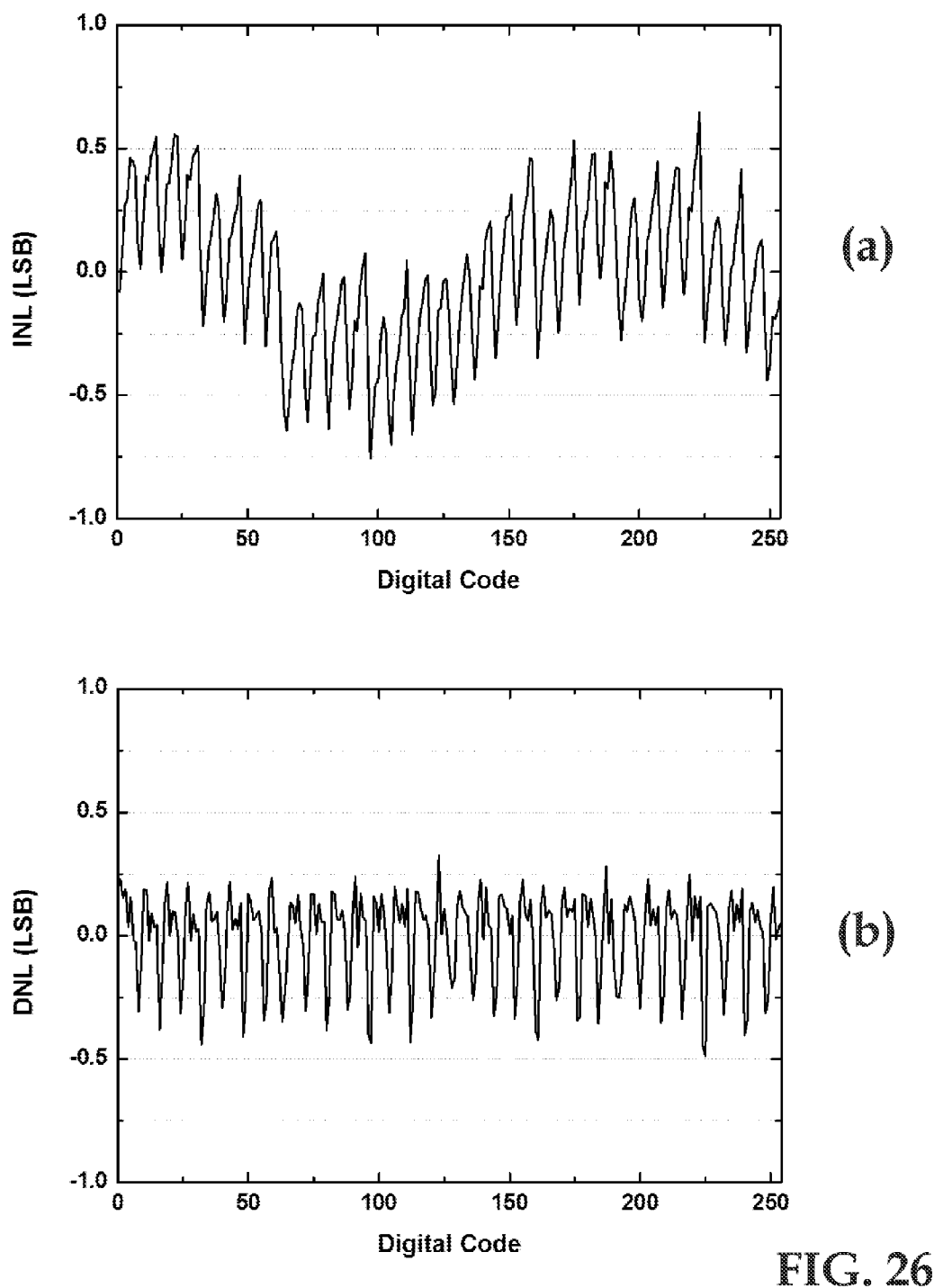
FIGS. 26(a) and (b) are graphs of INL/DNL for the ADC of FIG. 23.
FIGS. 26(c) and (d) are graphs of FFT output spectrums for the ADC of FIG. 23.
Figure 26:
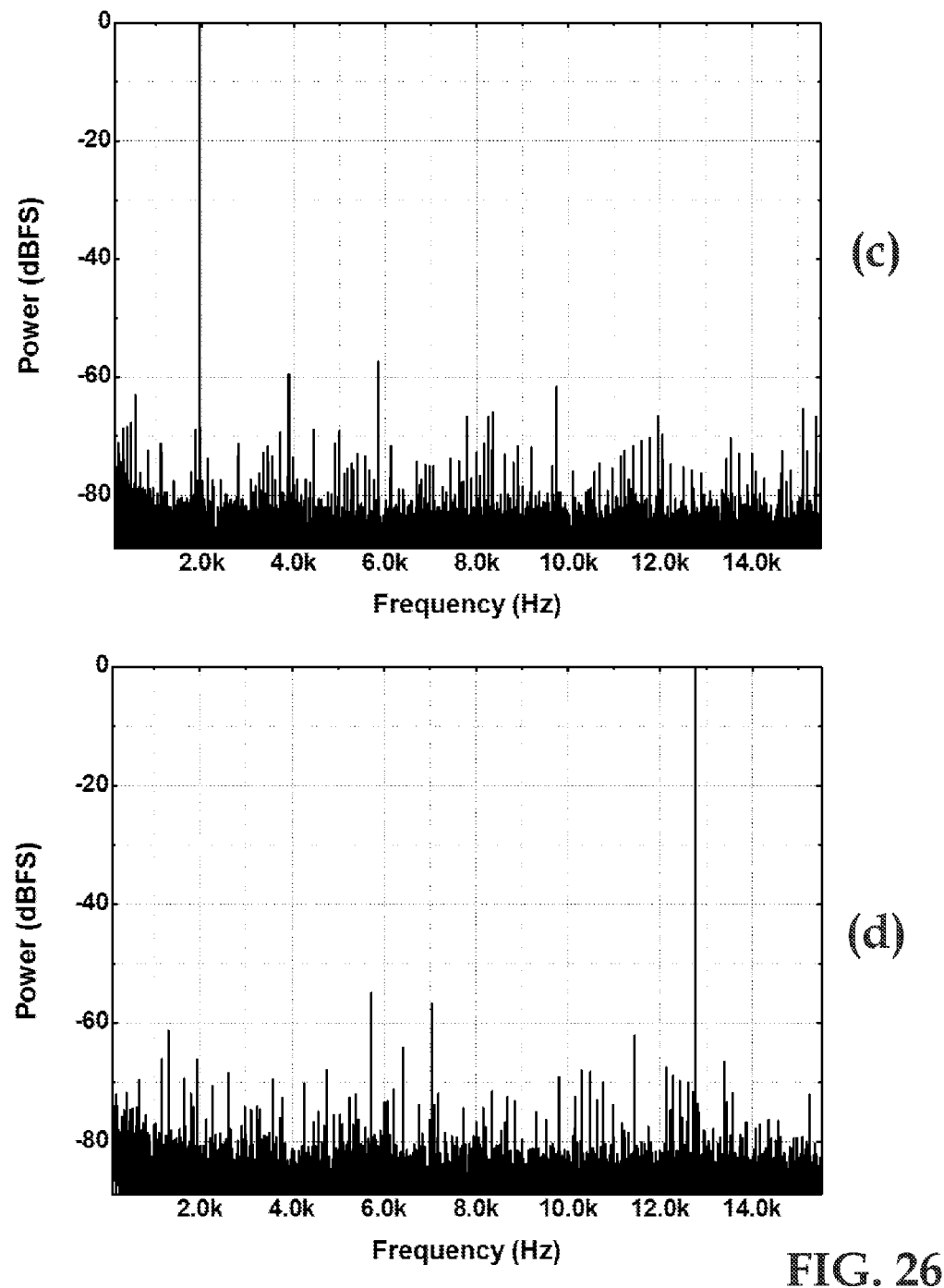
Figure 27:
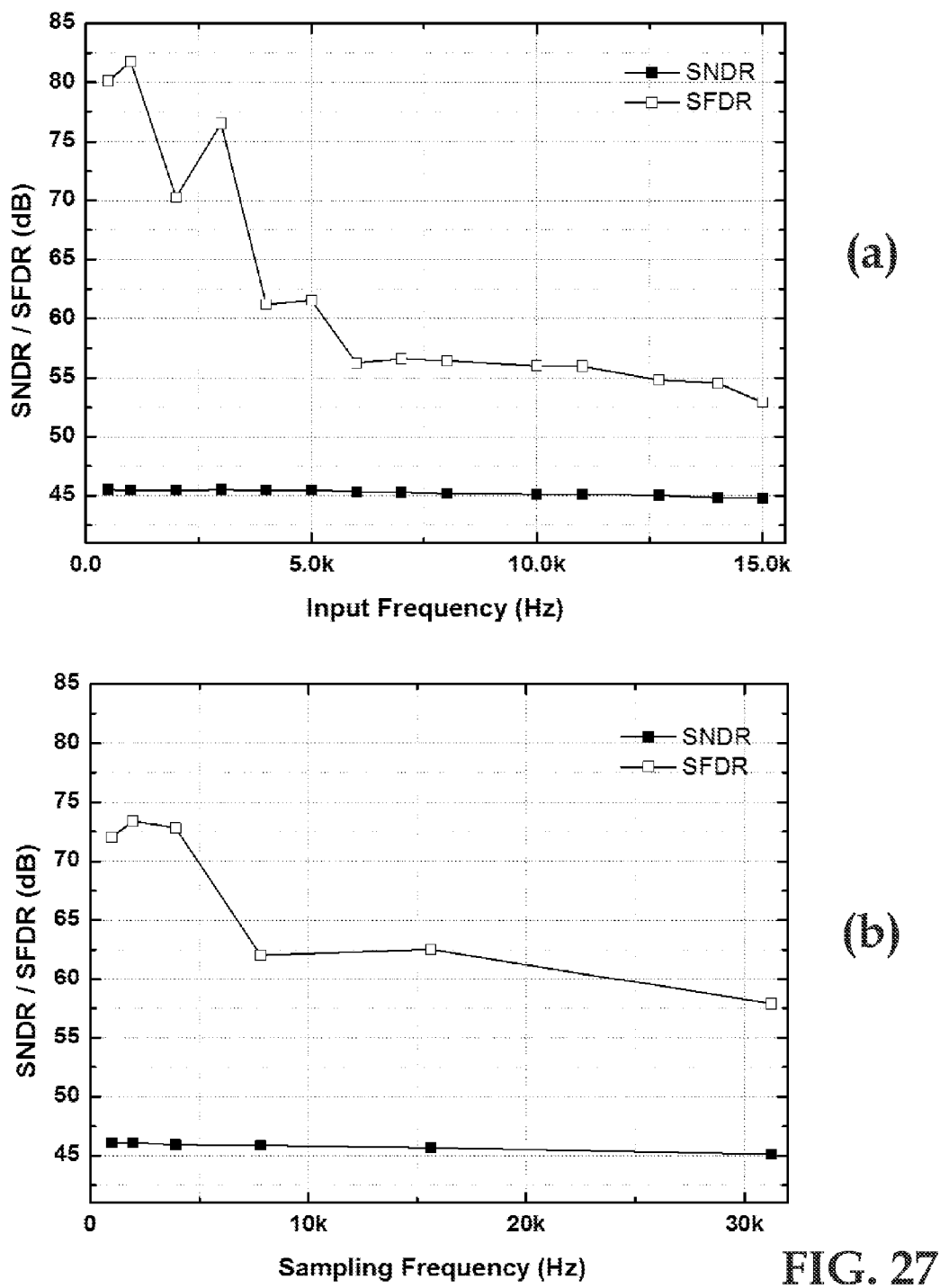
FIGS. 27(a) and (b) are graphs of SNDR/SFDR as a function of input and sampling frequencies, respectively, for the ADC of FIG. 23.
FIG. 27(c) is a graph of power consumption as a function of sampling frequency for 0.5v rail-to-rail operation of the ADC of FIG. 23.
FIG. 27(d) is a graph of SNDR for the over-the-rail operation of the ADC of FIG. 23 for various input levels and frequencies.
Figure 27:
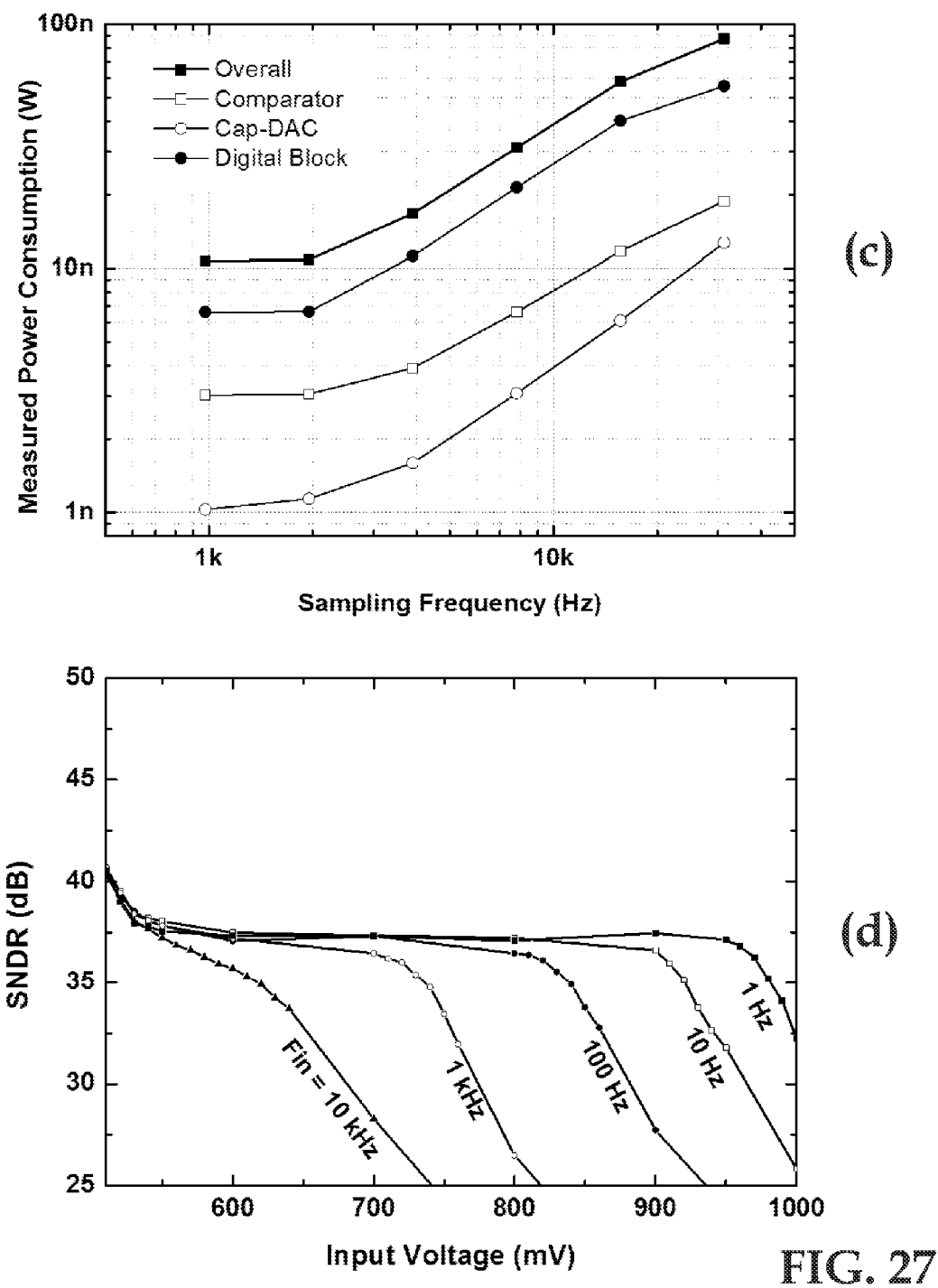

The prototype ADC 200 was fabricated in 0.25 µm 1P5M CMOS technology. The ADC core occupies 228×180 µm² with a unit capacitance of 49 fF. The measured INL/DNL and FFT spectrums for 1.9474 kHz and 12.7621 kHz input signals at 31.25 kS/s are shown in FIGS. 26(a)-(d). The INL and DNL are 0.70/−0.75 LSB and 0.3/−0.5 LSB, respectively. FIGS. 27(a) and (b) shows SNDR/SFDR for various input and sampling frequencies. The measured SNDR is 45.14 dB for the Nyquist input signal at 31.25 kS/s. The power consumption of each block was measured. The measured total power consumption is 87.41 nW for 31.25 kS/s. As shown in FIG. 27(c), the stand-by current of digital blocks becomes dominant below the sampling frequency of 2 kS/s. FIG. 27(d) shows the measured SNDR for the over-the-rail operation up to 1V input range. The ADC 200 shows 7.21 ENOB and 20.1 fJ/conversion-step as FOM. FIG. 28 shows a microphotograph of the fabricated ADC.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A neural interface, comprising:
    a housing that includes a threaded body extending from an enlarged head having a tool-engageable surface for threading the housing into and out of a cranial bore;
    an electrode located at a free end of the threaded body; and
    an electronic circuit at least partially located within the enlarged head, wherein the electronic circuit includes a monolithic voltage/current (V/I) generator that is configured to supply voltage and current references and a separate inductive coil connected in circuit that is configured to supply operating power received from an impinging magnetic field, wherein the electrode is electrically coupled to the circuit, and wherein the circuit is configured to wirelessly transmit data received via the electrode.

2. A neural interface as defined in claim 1, wherein the threaded body has a length approximately equal to a length of the cranial bore such that the electrode contacts but does not transverse a meninges layer located below the cranial bore.

3. A neural interface as defined in claim 1, further comprising a battery contained in the housing, wherein the inductive coil is electrically coupled to the battery to recharge the battery using energy received from the impinging magnetic field.

4. A neural interface as defined in claim 1, wherein the circuit is configured to wirelessly transmit the data via intra-skin communication with another neural interface.

5. A neural interface as defined in claim 1, wherein the circuit is configured to wirelessly transmit the data via radio frequency transmission.

6. A neural interface as defined in claim 1, wherein the electrode is mounted at the free end of the threaded body.

7. A neural interface as defined in claim 1, wherein the electrode comprises a flexible array of a plurality of electrodes that are wired into the threaded body at the free end.

8. A neural interface as defined in claim 1, wherein the electronic circuit includes an analog front end circuit, a modulator, and a transmitter.

9. A neural interface as defined in claim 8, wherein the electronic circuit includes a plurality of input channels and a separate analog front end circuit for each of the channels.

10. A neural interface as defined in claim 8, wherein the analog front end includes a preamplifier having floating-body transistor used as an input transistor of the preamplifer.

11. A neural interface as defined in claim 8, wherein the analog front end includes a preamplifier and a successive approximation register analog to digital converter (SAR ADC).

12. A neural interface as defined in claim 11, wherein the SAR ADC comprises a rail-to-rail SAR ADC.

13. A neural interface as defined in claim 11, wherein the SAR ADC is configured to operate in a rail-to-rail mode in which it provides n bits of data and in an over-the-rail mode in which it provides n+1 bits of data.

14. A neural interface as defined in claim 1, wherein the electronic circuit comprises an application-specific integrated circuit (ASIC).

15. A neural interface system comprising a plurality of the neural interfaces of claim 1.

16. A neural interface system as defined in claim 15, wherein at least one of the plurality of neural interfaces is configured to communicate wirelessly with one or more others of the neural interfaces and communicate wirelessly with an external device.

17. A neural interface system as defined in claim 16, wherein the plurality of neural interfaces are located in individual cranial bores clustered in close proximity to each other.

18. A neural interface system as defined in claim 17, wherein the tool-engageable surface comprises a hexagonal outer perimeter of the head, and wherein the plurality of neural interfaces comprise seven neural interfaces including six of the neural interfaces clustered around the seventh neural interface with each of the six being positioned adjacent one side of the hexagonal perimeter of the head.

19. A neural interface, comprising:
    a housing that includes a threaded body extending from an enlarged head having a tool-engageable surface for threading the housing into and out of a cranial bore;
    an electrode located at a free end of the threaded body; and
    an electronic circuit at least partially located within the enlarged head, wherein the electronic circuit includes an analog front end circuit including a preamplifier and a successive approximation register analog to digital converter (SAR ADC) configured to operate in a rail-to-rail mode in which it provides n bits of data and in an over-the-rail mode in which it provides n+1 bits of data, wherein the electrode is electrically coupled to the circuit, and wherein the circuit is configured to wirelessly transmit data received via the electrode.

20. A neural interface as defined in claim 1, wherein the monolithic V/I generator comprises a digitally-controllable monolithic V/I generator.

* * * * *